(12) United States Patent  
Powell et al.

(10) Patent No.: US 9,381,590 B2  
(45) Date of Patent: Jul. 5, 2016

(54) IMPLANTABLE MEDICAL DEVICE FEEDTHROUGHS AND HOUSINGS

(71) Applicants: Anthony Powell, Bondi Junction (AU); Graham Ball, Greenwich (AU); Melvyn Clarke, Balgowlah (AU); Charles Roger Aaron Leigh, Epping (AU); Grahame Walling, Newport (AU); Kenny Crichton, Chatswood (AU)

(72) Inventors: Anthony Powell, Bondi Junction (AU); Graham Ball, Greenwich (AU); Melvyn Clarke, Balgowlah (AU); Charles Roger Aaron Leigh, Epping (AU); Grahame Walling, Newport (AU); Kenny Crichton, Chatswood (AU)

(73) Assignee: Cochlear Limited, Macquarie University, NSW (AU)

( * ) Notice: Subject to any disclaimer, the term of this patent is extended or adjusted under 35 U.S.C. 154(b) by 350 days.

(21) Appl. No.: 13/918,228

(22) Filed: Jun. 14, 2013

(65) Prior Publication Data

US 2014/0371835 A1    Dec. 18, 2014

(51) Int. Cl.
    *B23K 1/00*      (2006.01)
    *B23K 1/19*      (2006.01)
    *A61N 1/375*      (2006.01)

(52) U.S. Cl.
    CPC ............ *B23K 1/0008* (2013.01); *A61N 1/3754* (2013.01); *B23K 2203/18* (2013.01)

(58) Field of Classification Search
    CPC ............. A61N 1/3754; A61N 1/36032; B23K 1/0008; H01G 4/35; H01G 2/103
See application file for complete search history.

(56) References Cited

U.S. PATENT DOCUMENTS

| | | | |
|---|---|---|---|
| 4,217,137 A | 8/1980 | Kraska et al. | |
| 4,940,858 A | 7/1990 | Taylor et al. | |
| 6,410,161 B1 | 6/2002 | Li | |
| 6,903,268 B2 | 6/2005 | Marshall et al. | |
| 6,935,549 B2 | 8/2005 | Wolf | |
| 7,132,173 B2 | 11/2006 | Daulton | |
| 7,145,076 B2 | 12/2006 | Knappen et al. | |
| 7,498,516 B1 * | 3/2009 | He .................... | A61N 1/3754 174/94 R |
| 7,527,187 B2 | 5/2009 | Pohlman | |
| 8,186,564 B1 | 5/2012 | Collinsworth et al. | |
| 2007/0183118 A1 | 8/2007 | Fu et al. | |
| 2009/0292337 A1 | 11/2009 | Capcelea et al. | |
| 2010/0326723 A1 | 12/2010 | McCusker et al. | |
| 2011/0059331 A1 | 3/2011 | Smith et al. | |
| 2012/0012374 A1 | 1/2012 | Koester et al. | |
| 2013/0100595 A1 | 4/2013 | Koester et al. | |

FOREIGN PATENT DOCUMENTS

WO      2012082901 A2    6/2012

\* cited by examiner

*Primary Examiner* — Erin Saad
(74) *Attorney, Agent, or Firm* — Edell, Shapiro & Finnan, LLC

(57) ABSTRACT

Embodiments are generally directed to a feedthrough for an implantable medical device. The feedthrough comprises an insulator having one or more conductors extending therethrough that is hermetically connected (joined) to a housing of the implantable medical device. More specifically, the housing includes an aperture and the insulator is configured be positioned in the aperture. Braze material is configured to be positioned in one or more indentations in at least one of the housing or the insulator such that the braze material is disposed in the indentations between the insulator and the housing.

20 Claims, 37 Drawing Sheets

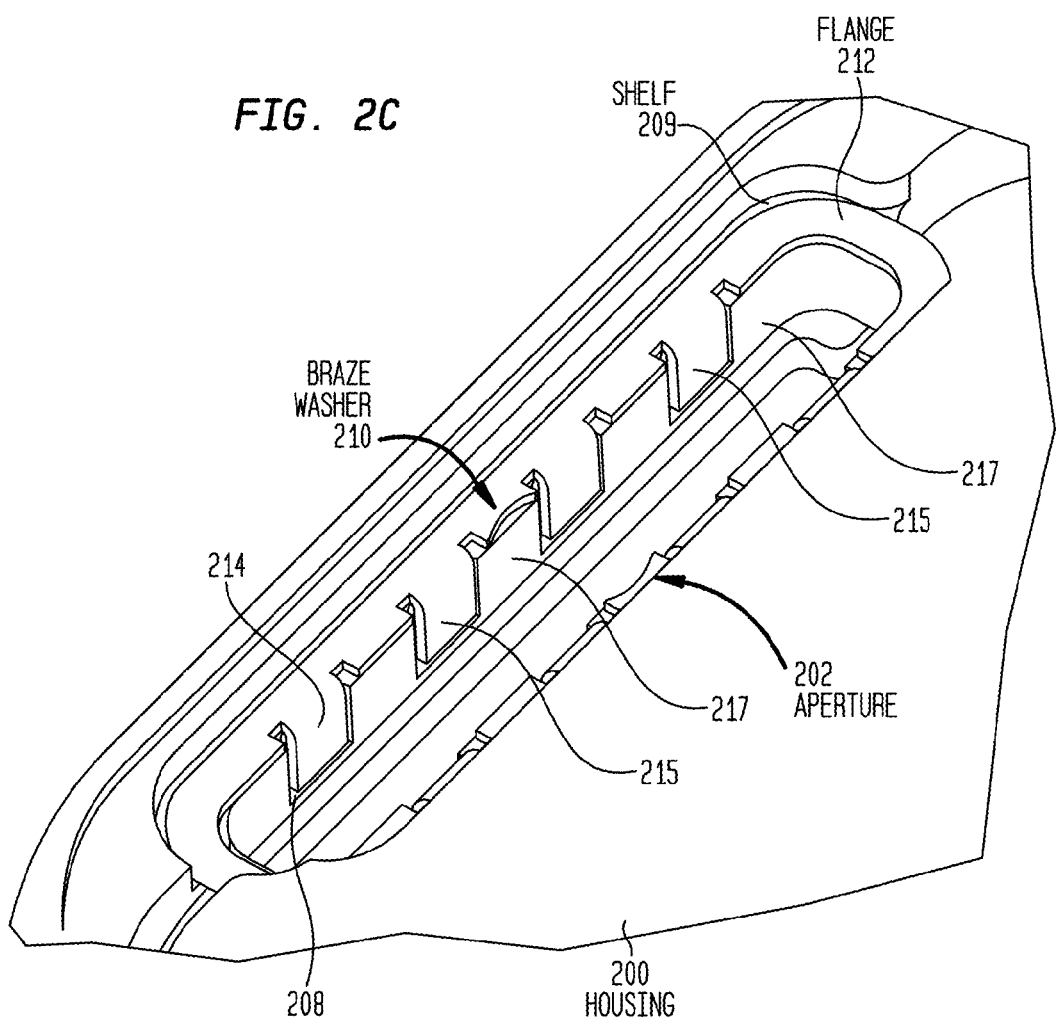

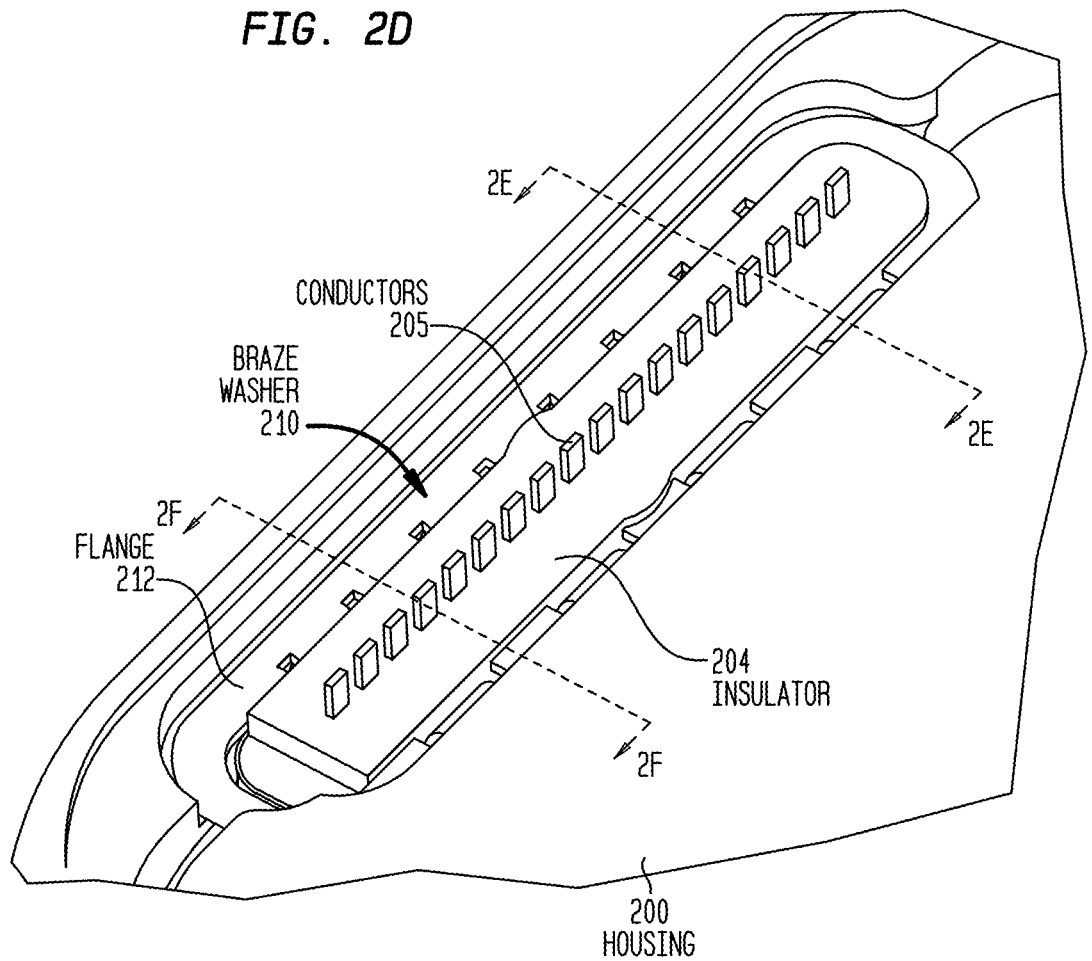

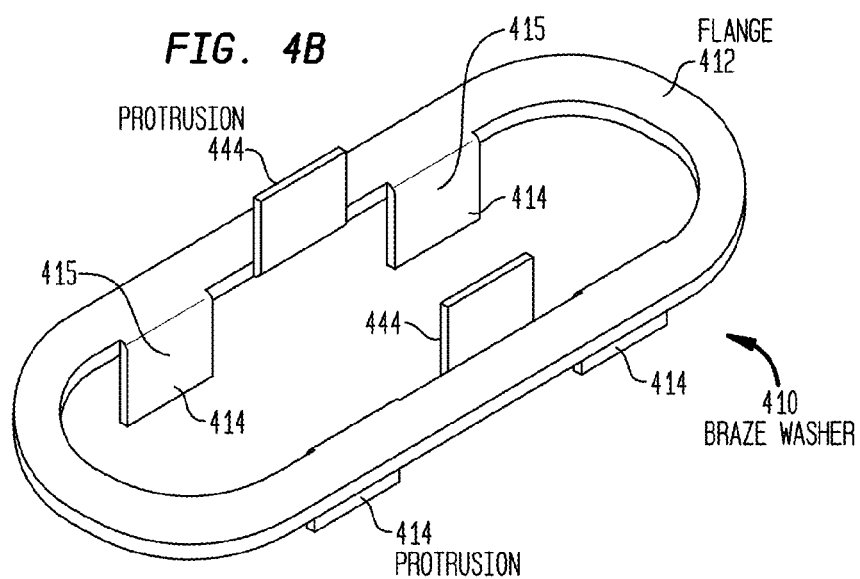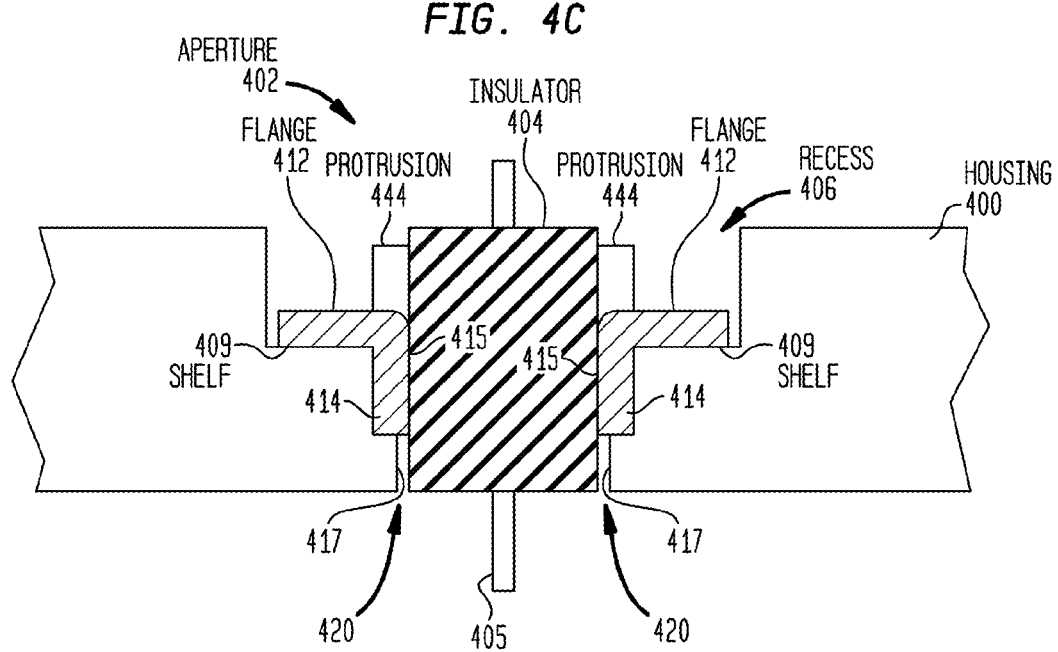

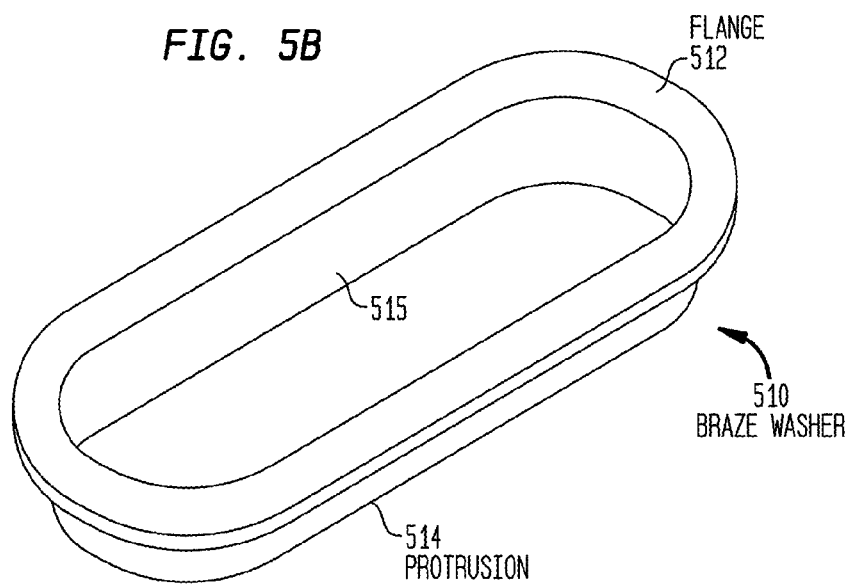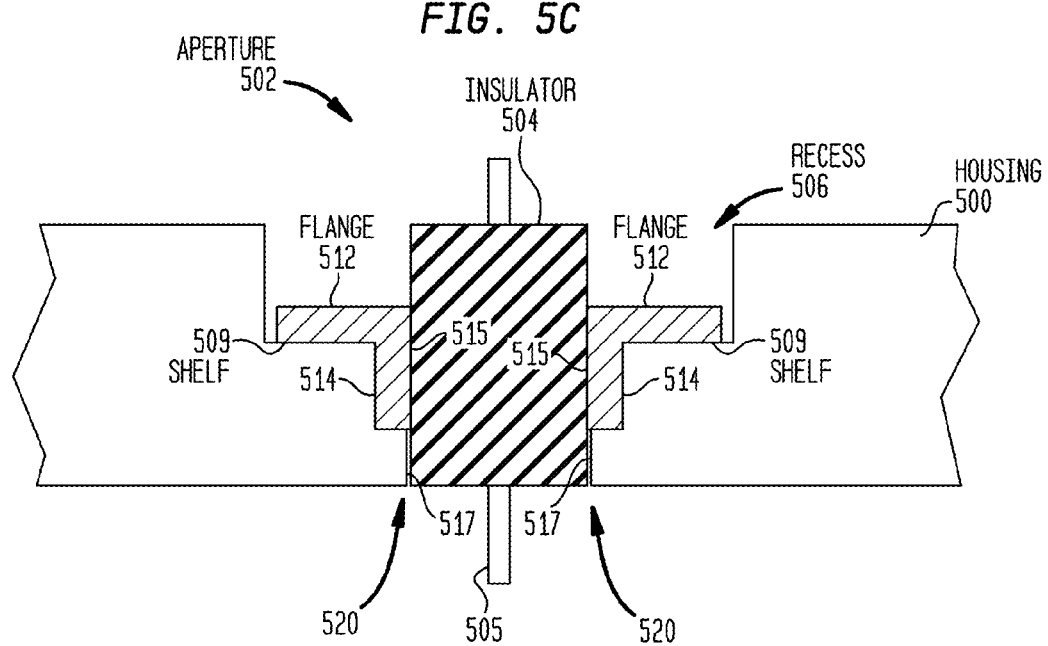

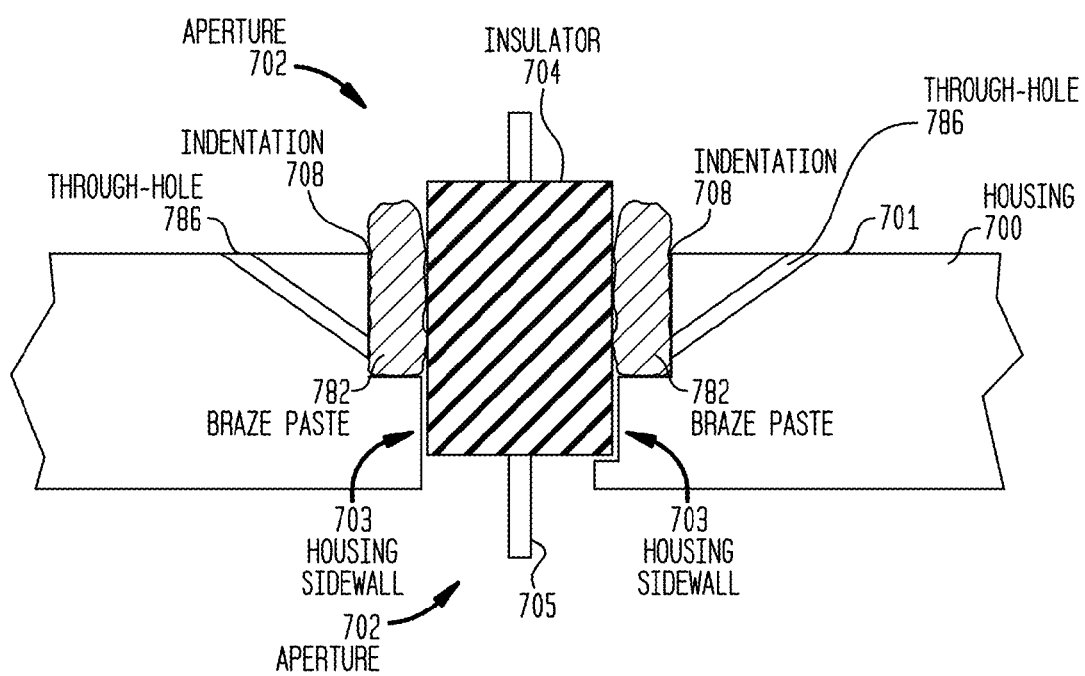

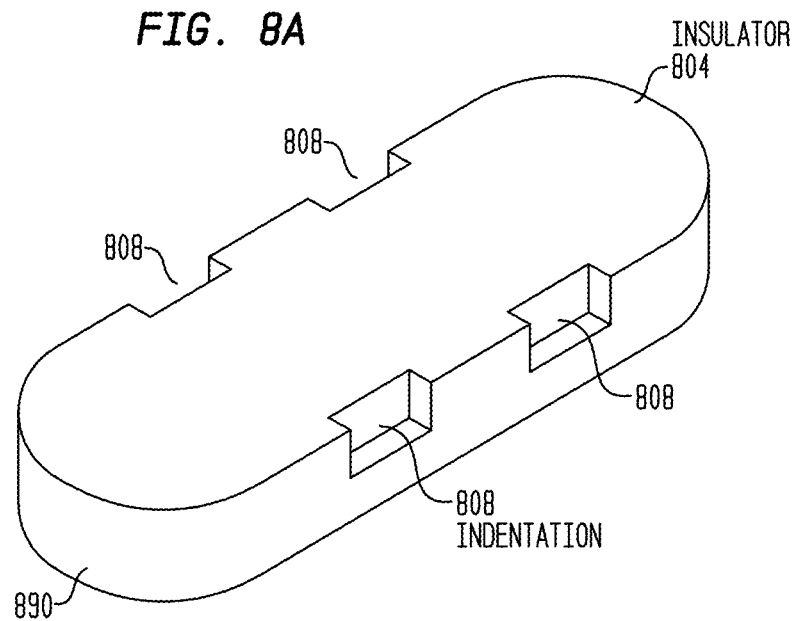

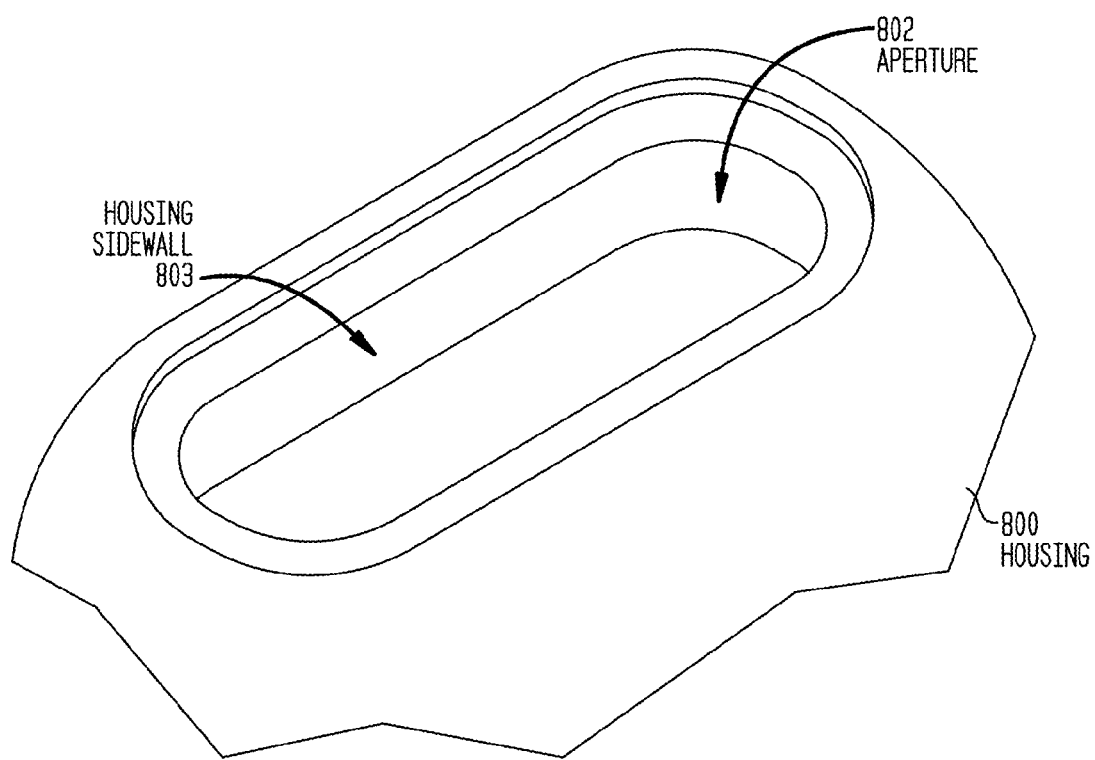

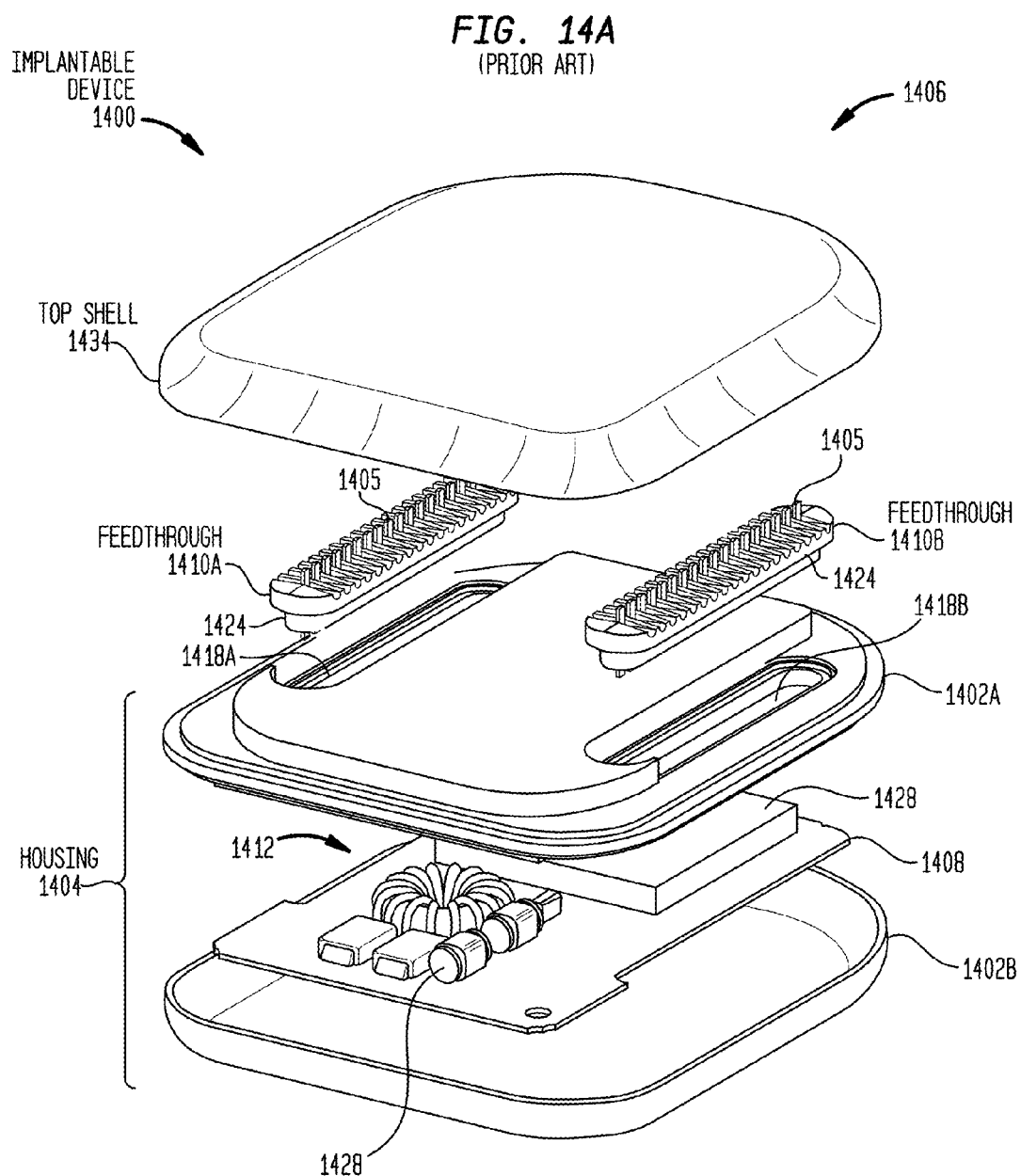

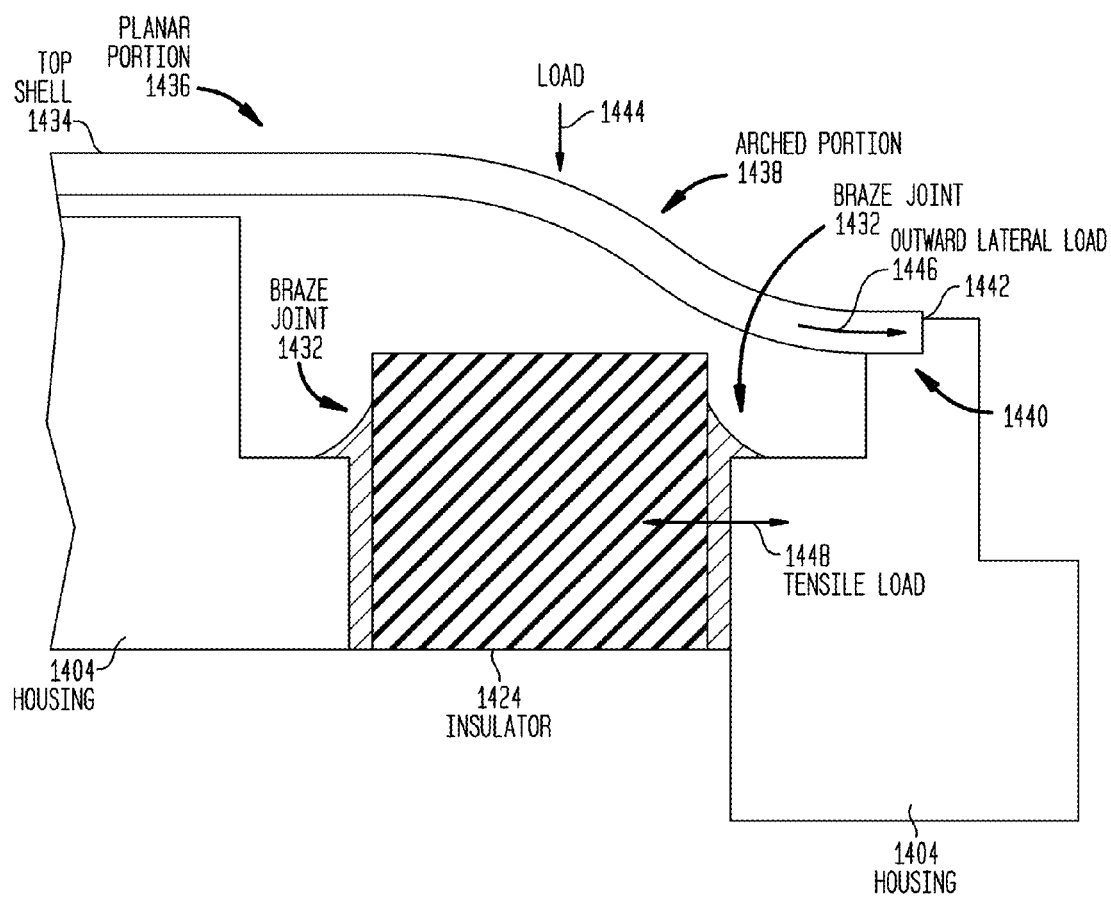

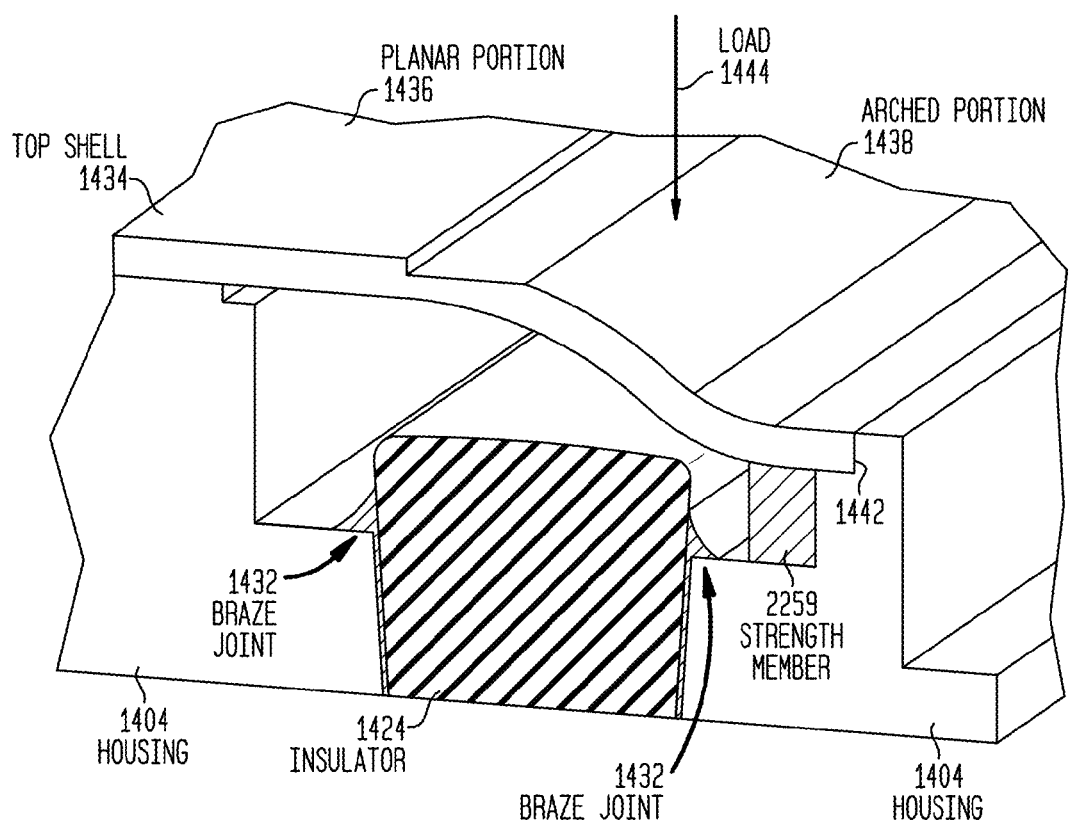

IMPLANTABLE MEDICAL DEVICE
FEEDTHROUGHS AND HOUSINGS

BACKGROUND

1. Field of the Invention

The present invention relates generally to implantable medical devices.

2. Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

SUMMARY

In one aspect of the invention, an apparatus is provided. The apparatus comprises a housing having an aperture extending through the housing, wherein a housing sidewall substantially surrounds the aperture, an insulator configured to be positioned in the aperture and comprising one or more conductors extending therethrough, and braze material configured to be positioned in one or more indentations in at least one of the housing sidewall and the insulator such that the braze material is disposed in the indentations between the insulator and the housing sidewall In another aspect of the present invention, a method is provided. The method comprises forming a housing that includes an aperture extending through the housing, wherein a housing sidewall substantially surrounds the aperture, positioning an insulator comprising one or more conductors extending therethrough in the aperture, positioning braze material in one or more indentations in at least one of the housing sidewall and the insulator such that the braze material is disposed in the indentations between the insulator and the housing sidewall, and applying heat to melt the braze material so as to form a hermetic joint between the insulator and the housing.

In a further aspect of the invention, an apparatus is provided. The apparatus comprises a housing having an aperture extending through the housing, wherein a housing sidewall substantially surrounds the aperture, braze material initially positioned adjacent to the aperture at a surface of the housing, and an insulator configured to be positioned in the aperture and joined to the housing via brazing that results in melting and flow of the braze material. The insulator comprises one or more conductors extending therethrough from a first surface to a second surface, and one or more braze-impediment features disposed on a cross-surface connecting the first surface to the second surface at a location between an initial position of the braze material and the first surface and configured to prevent melted braze material from flowing onto the first surface

BRIEF DESCRIPTION OF THE DRAWINGS

Embodiments of the present invention are described herein in conjunction with the accompanying drawings, in which:

FIG. 2C is a perspective view of the braze washer of FIG. 2B and the implantable housing of FIG. 2A;

FIG. 2D is a perspective view of the braze washer of FIG. 2B, the implantable housing of FIG. 2A, and an insulator in accordance with embodiments presented herein;

FIG. 4B is a perspective view of a braze washer in accordance with embodiments presented herein;

FIG. 4C is a cross-sectional view of the braze washer of FIG. 4B, the implantable housing of FIG. 4A, and an insulator in accordance with embodiments presented herein;

FIG. 5B is a perspective view of a braze washer in accordance with embodiments presented herein;

FIG. 5C is a cross-sectional view of the braze washer of FIG. 5B, the implantable housing of FIG. 5A, and an insulator in accordance with embodiments presented herein;

FIG. 7 is a cross-sectional view of a braze washer, an implantable housing, and an insulator in accordance with embodiments presented herein;

FIG. 8A is a perspective view of an insulator in accordance with embodiments presented herein;

FIG. 8B is a perspective view of a portion of an implantable housing in accordance with embodiments presented herein;

FIG. 14A is an exploded view of a conventional implantable medical device;

FIG. 14B is a cross-sectional view of a portion of the implantable medical device of FIG. 14A;

FIG. 22C is cross-sectional, perspective view of a portion of an implantable medical device in accordance with embodiments presented herein.

DETAILED DESCRIPTION

Embodiments are generally directed to a feedthrough for an implantable medical device. The feedthrough comprises an insulator having one or more conductors extending therethrough that is hermetically connected (joined) to a housing of the implantable medical device. More specifically, the housing includes an aperture and the insulator is configured be positioned in the aperture. Braze material is configured to be positioned in one or more indentations in at least one of the housing or the insulator such that the braze material is disposed in the indentations between the insulator and the housing.

For ease of illustration, embodiments are primarily described herein with connection to an implantable component of a cochlear implant (also commonly referred to as cochlear implant device, cochlear prosthesis, and the like; simply "cochlear implant" herein). However, it is to be appreciated that embodiments may be used in conjunction with different implantable medical devices including other hearing prostheses (e.g., auditory brain stimulators, mechanical stimulators, etc.), sensors, implantable pacemakers, defibrillators, functional electrical stimulation devices, catheters, etc.

Figure 1:
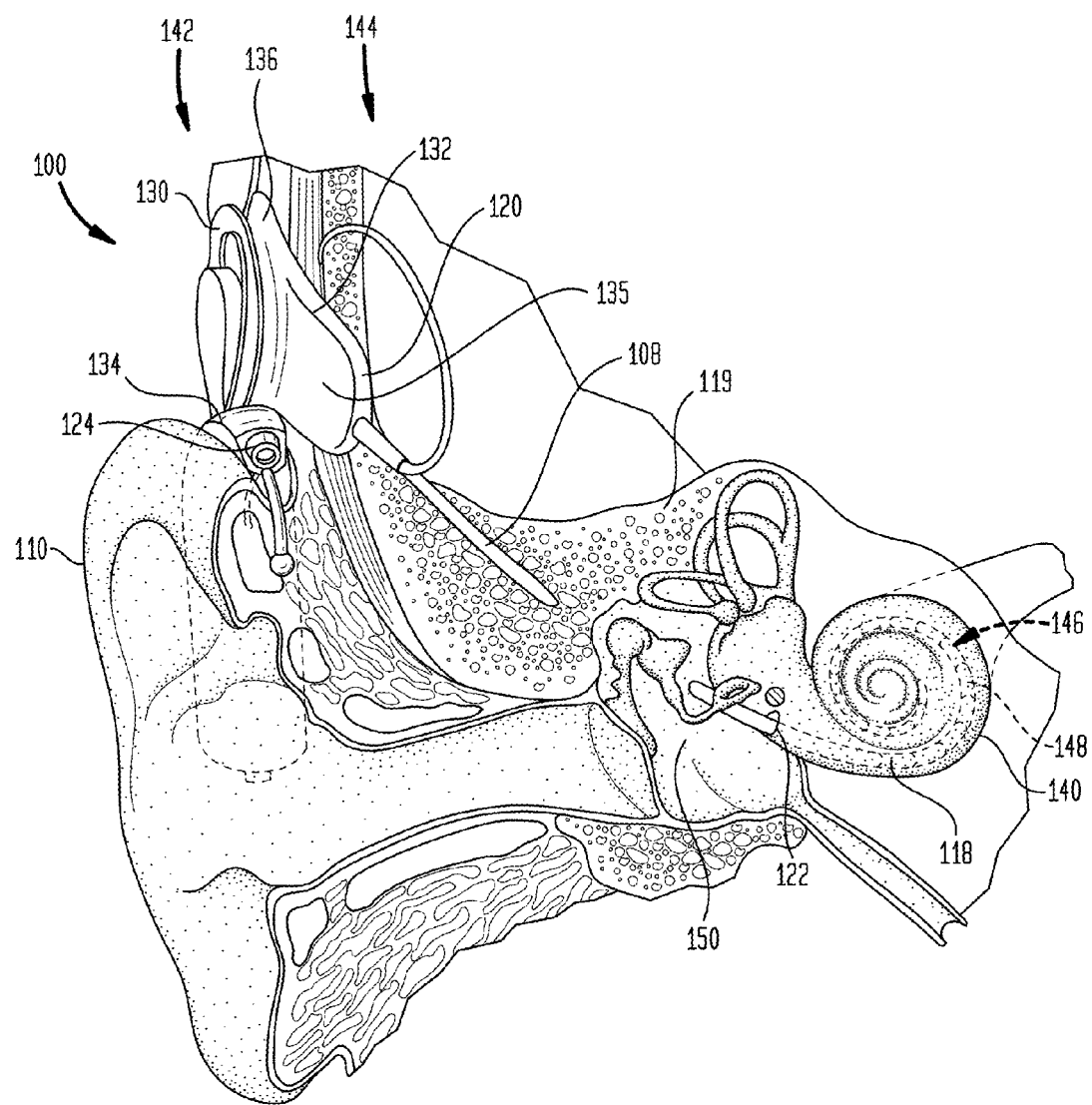
FIG. 1 is a schematic diagram of an implantable medical device that may be used in conjunction with embodiments presented herein.

FIG. 1 is perspective view of an exemplary cochlear implant 100 in which embodiments presented herein may be implemented. The cochlear implant 100 comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), an external coil 130 and, generally, a magnet (not shown) fixed relative to the external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. The transceiver unit 132 is connected to an internal coil 136 and, generally, a magnet (not shown) fixed relative to the internal coil 136.

The magnets in the external component 142 and internal component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is implanted in cochlea 140 and includes a contact array 146 comprising a plurality of stimulating contacts 148. Stimulating assembly 118 extends through cochleostomy 122 and has a proximal end connected to stimulator unit 120 via lead region 108 that extends through mastoid bone 119.

Internal transceiver unit 132 and stimulator unit 120 are disposed in a hermetically-sealed and biocompatible housing 135. The housing 135 operates as a protective barrier between the electrical components (e.g., in transceiver unit 132 and stimulator unit 120) and the recipient's tissue and bodily fluid. Prior to implantation, the housing 135 and the internal coil 136 may be overmolded or coated with a silicone elastomer to create a uniform compliant surface suitable for implantation.

As noted above, cochlear implant 100, similar to other implantable medical devices, includes one or more electrical components positioned in the hermetic housing 135. There is a need to transfer electrical signals to and/or from these electrical components and one or more components positioned outside (external to) the housing 135. For example, in the embodiments of FIG. 1, the stimulating contacts 148 in stimulating assembly 118 (outside the housing 135) receive electrical signals from the stimulator unit 120 (inside the housing 135). Similarly, the internal coil 136 (outside the housing 135) transfers signals to, and possibly receives signals from, the transceiver unit 132 (inside the housing 135). As such, cochlear implant 100 includes a hermetic feedthrough (not shown in FIG. 1) that provides a physical electrical connection through the housing that is used to transfer signals to/from the electrical components outside of the housing to the electrical components within the housing.

Hermetic feedthroughs are one of the most complex mechanical structures in an implantable medical device and typically include an insulator (e.g., formed from ceramic) and one or more conductors (e.g., formed from platinum) that extend through the insulator. The insulator is positioned in an aperture of the housing, and then joined to the housing via one or more braze joints. The braze joints are formed from a brazing material that may comprise, for example, a Titanium brazing Alloy (e.g., titanium-copper-nickel foil (TiCuNi), gold, etc.

Brazing is a joining process where a filler or braze metal is heated above its melting point (while protected by a suitable atmosphere such as flux) so as to be distributed between two or more close-fitting parts. The flow of the braze material over the two close-fitting parts is known as "wetting." In conventional arrangements, braze material flows between the two close-fitting parts via capillary action. As known, capillary attraction refers to the ability of a liquid to flow in narrow spaces without the assistance of, and in opposition to external forces like gravity. Capillary action occurs due to inter-molecular attractive forces between the liquid and the solid surrounding surfaces.

Presented herein are braze joints and braze joining techniques that do not rely solely on capillary action to ensure that braze material flows between two close fitting parts. More specifically, in accordance with certain embodiments braze material is positioned between two close-fitting prior to brazing in a manner that does not overly enlarge the distance between the two close fitting parts.

Figure 2A:
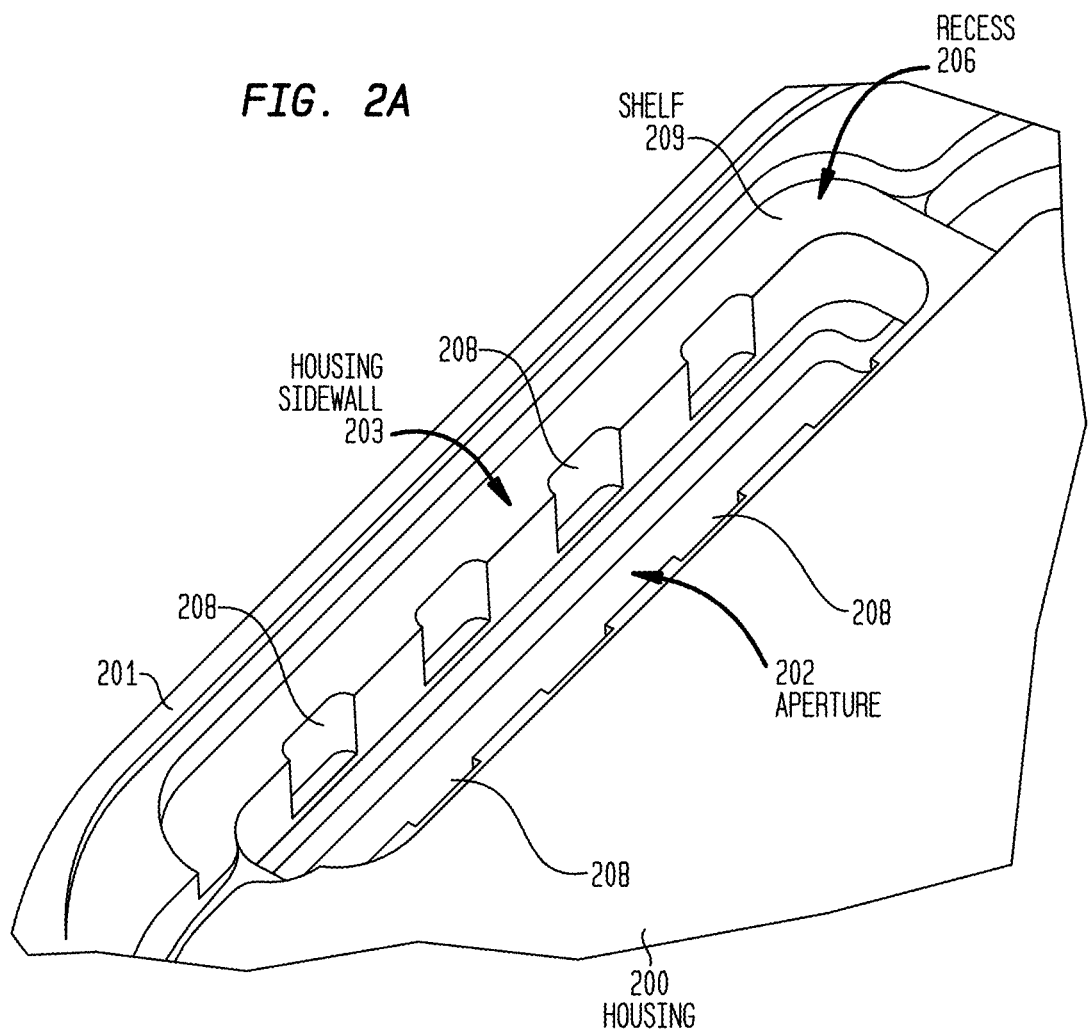
FIG. 2A is a perspective view of a portion of an implantable housing in accordance with embodiments presented herein.

FIGS. 2A-2F illustrate elements of an elongate feedthrough that includes a braze joint in accordance with embodiments presented herein. More specifically, FIG. 2A is a perspective view of a portion of an implantable chassis or housing 200 of an implantable medical device (e.g., cochlear implant). The housing 200 may be formed from, for example, titanium, platinum, or other biocompatible material.

The housing 200 includes an elongate aperture 202 that extends through the housing. The aperture 202 is surrounded by a housing sidewall 203. The housing 200 includes a plurality of indentations or notches 208 that extend into the housing sidewall 203 from the aperture 202. In other words, a plurality of indentations 208 are disposed in the housing sidewall so as to be positioned around the aperture 202. In the embodiments of FIG. 2A, the housing 200 also includes an elongate recess 206 that forms a shelf 209 around a proximal end of the aperture 202 (i.e., the end of the aperture closest to outer surface 201 of the housing 200).

The aperture 202 is configured to receive an insulator 204 (FIG. 2D) that includes a plurality of conductors (pins) 205 extending therethrough. In order to ensure that the housing 200 provides a hermetic seal between electrical components inside the housing 200 and the recipient's tissue and bodily fluid, the insulator 204 is joined to the housing 200 through brazing. As noted, brazing is a joining process where braze metal is heated above its melting point so as to be distributed between two or more close-fitting parts. In the case of a feedthrough, the close-fitting parts are the insulator 204 positioned in the aperture 202 and the housing 200, more specifically the housing sidewall 203, surrounding the aperture 202.

After braze material flows between the insulator 204 and the housing sidewall 203, the braze material is cooled so as to harden and hermetically join the insulator 204 to the housing 200.

Figure 2B:
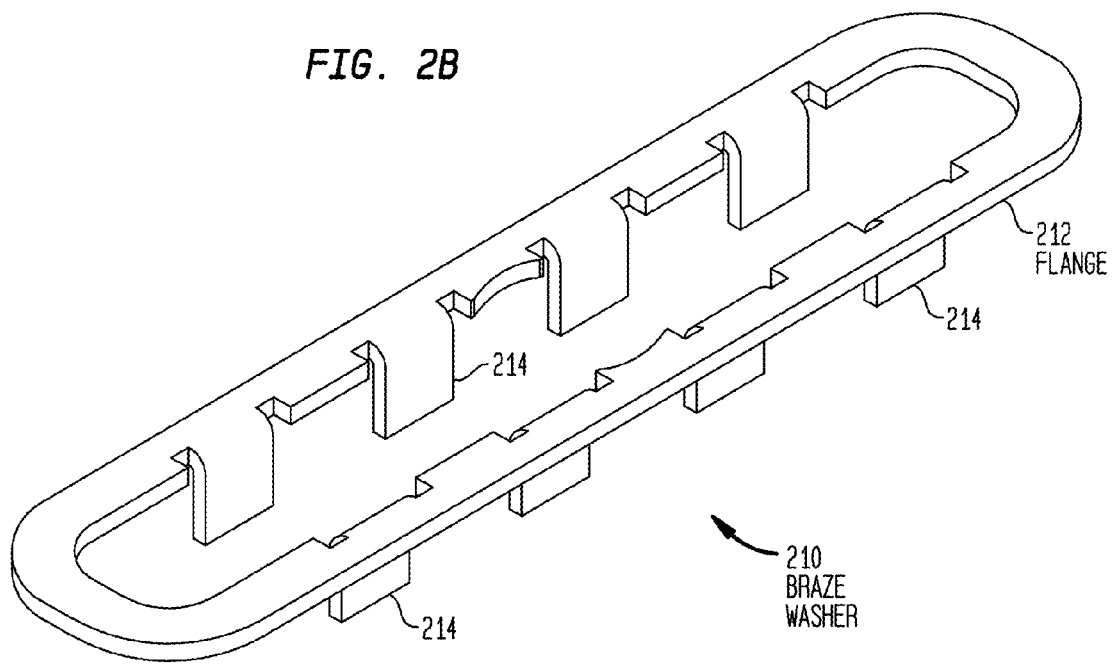
FIG. 2B is a perspective view of a braze washer in accordance with embodiments presented herein.

In order to perform the brazing, the braze material is first positioned in proximity to the insulator 204 and the housing 200. In accordance with certain embodiments presented herein, the braze material is in the form of a braze washer. FIG. 2B is a perspective view of an exemplary braze washer 210. As shown, the braze washer 210 includes an elongate top flange 212 and a plurality of protrusions or tabs 214 that extend from the top flange.

The braze washer 210 is configured to be inserted into the aperture 202 and mate with the housing 200. More specifically, as shown in FIG. 2C, the flange 212 is configured to abut (i.e., seat against) a surface of the housing 200. In the embodiments of FIG. 2C, the flange 212 abuts the shelf 209 created by recess 206. In alternative embodiments, the recess 206 may be omitted and the flange 212 may abut the outer surface 201 of the housing 200. Additionally, when the braze washer 210 is inserted into the aperture 202, the braze protrusions 214 are positioned in the indentations 208. Outer surfaces 215 of the braze protrusions 214 may be substantially aligned with (i.e., substantially even with) the surfaces 217 of the housing sidewall 203 between indentations 208.

Figure 2E:
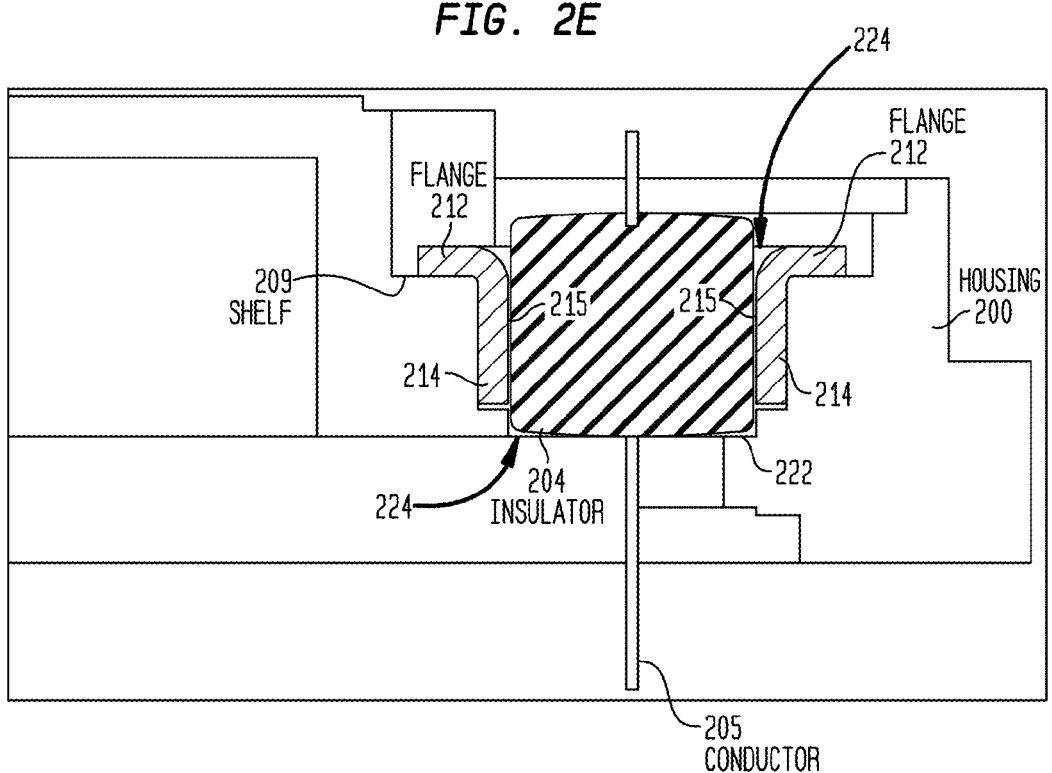
FIGS. 2E and 2F are cross-sectional views of the arrangement of FIG. 2D.
Figure 2F:
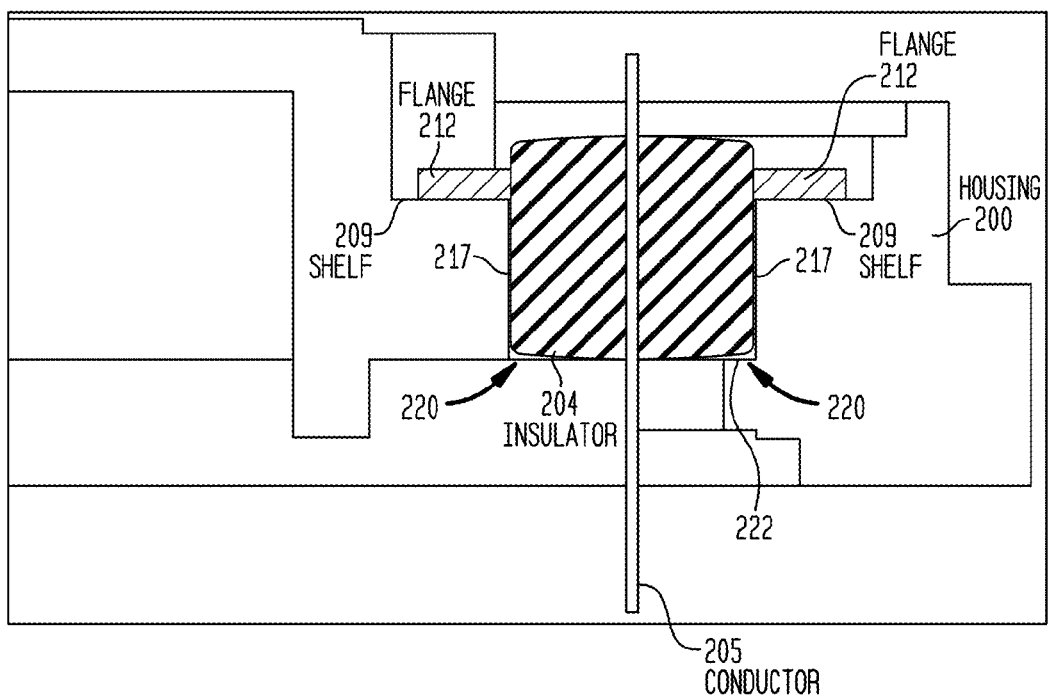

FIG. 2D is a perspective view illustrating insulator 204 positioned in aperture 202. FIG. 2E is a cross-sectional view along line 2E-2E of FIG. 2D, while FIG. 2F is a cross-sectional view along line 2F-2F of FIG. 2D.

As shown, the insulator 204 is configured to substantially fill the aperture 202 so as to be in close proximity to the surfaces 217 and the surfaces 215. In general, a small gap 220 will be present between the insulator 204 and surfaces 217. The gap 220 may, for example, have a width of several microns. The insulator 204 may be in contact with surfaces 215 of protrusions 214 or spaced from the protrusions by a gap 224. The gap 224 may be the same or different width as gap 220. In summary, when the insulator 204 is inserted into the aperture 202, the braze protrusions 214 will be positioned between the insulator 204 and the housing sidewall 200.

When the braze washer 210 and insulator 204 are positioned in housing 200, heat is applied to melt the braze washer 210. Because the protrusions 214 of the braze washer 210 are positioned between the insulator 204 and the housing sidewall 203 (i.e., the close-fitting parts), the embodiments of FIGS. 2A-2F do not rely solely on capillary action to position braze material between the close-fitting parts (the insulator 204 and the housing sidewall 203).

In summary, the embodiments of FIGS. 2A-2F locate a small amount of braze material within the aperture 202 (i.e., the protrusions 214 between the housing 200 and the insulator 204) supplemented by additional material adjacent to the aperture (flange 212). This arrangement provides for optimum heat transfer between the braze material and the close-fitting parts, thereby leading to efficient wetting. In these embodiments, the resulting braze joint has only localized (discrete) enlargements of the joint (i.e., enlargements at the protrusions/indentations) so as to retain strength advantages of a narrow joint.

In the embodiments of FIGS. 2E and 2F, the insulator 204 rests on a lip or ledge 222 of housing 200 during the brazing process. In alternative embodiments, the ledge 222 may be omitted.

In certain embodiments, braze washer 210 and/or housing 200 are designed such that the insulator 204 is press-fit into the aperture 202 and the braze washer 210. In such embodiments, when the insulator 204 is inserted into the aperture 202, a portion of the braze washer 210, such as protrusions 214, provides a small amount of resistance to the insulator 204 during insertion so as to retain the insulator 204 within the aperture prior to brazing. In certain embodiments, the protrusions 214 are sized such that the surfaces 215 of the braze protrusions 214 extend into the aperture 202 beyond the surfaces 217 so as to make contact with the insulator 204 as it is inserted into the aperture. In other embodiments, the protrusions 214 are oriented (e.g., tilted) so as extend into the aperture 202 as to make contact with the insulator 204 as it is inserted into the aperture.

It is to be appreciated that the embodiments of FIGS. 2A-2F are merely illustrative and that various modifications to the housing, braze material, insulator, etc. are possible in alternative embodiments presented herein. For example, FIGS. 3A-3D, 4A-4C, 5A-5C, 6, 7, and 8A-8B illustrate elongate feedthroughs in accordance with alternative embodiments presented herein.

Figure 3A:
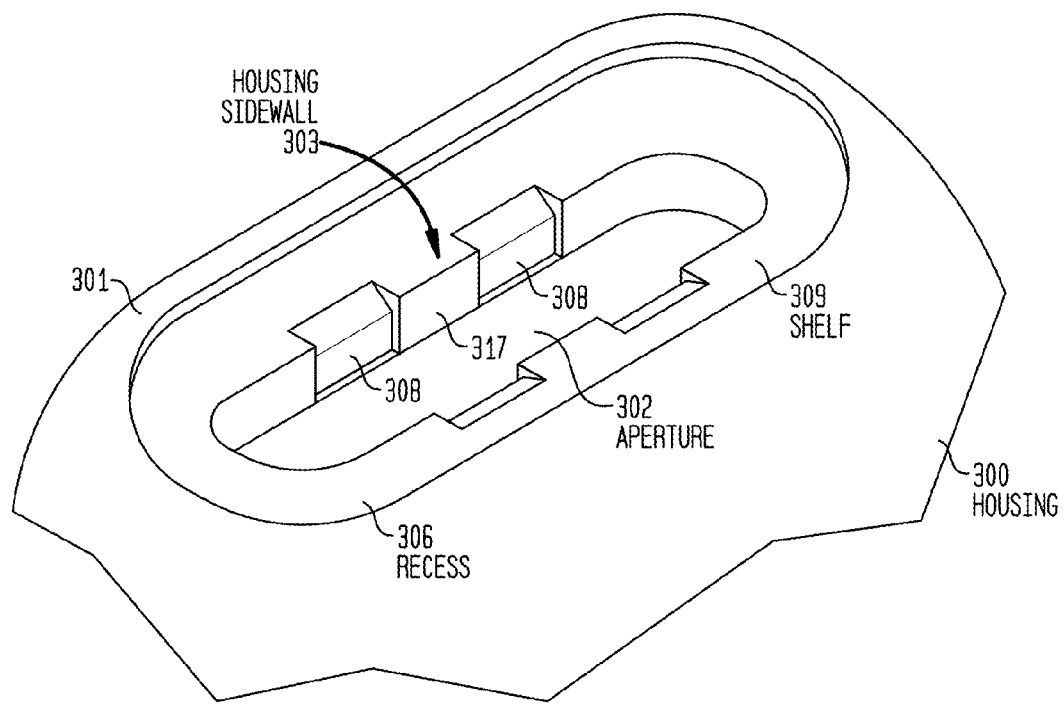
FIG. 3A is a perspective view of a portion of an implantable housing in accordance with embodiments presented herein.

More specifically, FIG. 3A is a perspective view of a portion of an implantable housing 300 of an implantable medical device. The housing 300 includes an elongate aperture 302 that extends through the housing 300 and that is substantially surrounded by a housing sidewall 303. The housing 300 also includes a plurality of indentations 308 that extend into the housing sidewall 303 from the aperture 302. As such, the indentations 308 are disposed around the aperture 302. In the embodiments of FIG. 3A, the housing 300 also includes an elongate recess 306 that forms a shelf 309 around a proximal end of the aperture 302 (i.e., the end of the aperture closes to an outer surface 301 of the housing 300).

The aperture 302 is configured to receive an insulator 304 (FIG. 3D) that includes a plurality of conductors 305 (FIG. 3D) extending therethrough. In order to ensure that the housing 300 provides a hermetic seal between electrical components inside the housing 300 and the recipient's tissue and bodily fluid, the insulator 304 is joined to the housing through brazing. That is, insulator 304 is configured to be positioned in the aperture 302 such that, when heated, braze material flows between the insulator 304 and the housing sidewall 303. When the braze material cools and hardens, the insulator 304 is hermetically joined to the housing 300.

Figure 3B:
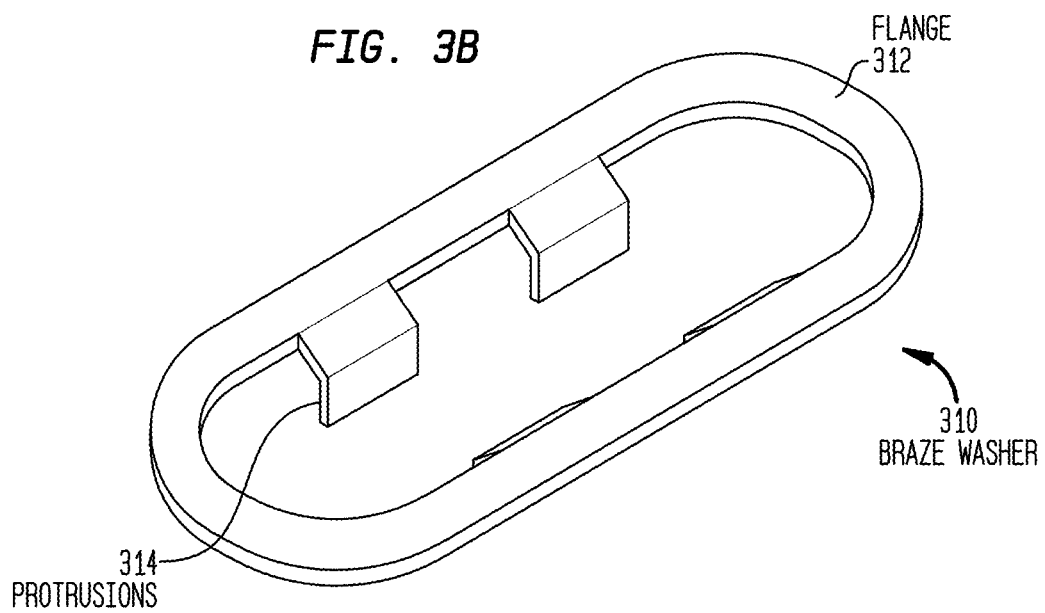
FIG. 3B is a perspective view of a braze washer in accordance with embodiments presented herein.

In order to perform the brazing, the braze material is first positioned in proximity to the insulator 304 and the housing 300. In accordance with certain embodiments presented herein, the braze material is in the form of a braze washer. FIG. 3B is a perspective view of an exemplary braze washer 310. As shown, the braze washer 310 includes an elongate top flange 312 and a plurality of protrusions 314 that extend from the flange.

Figure 3C:
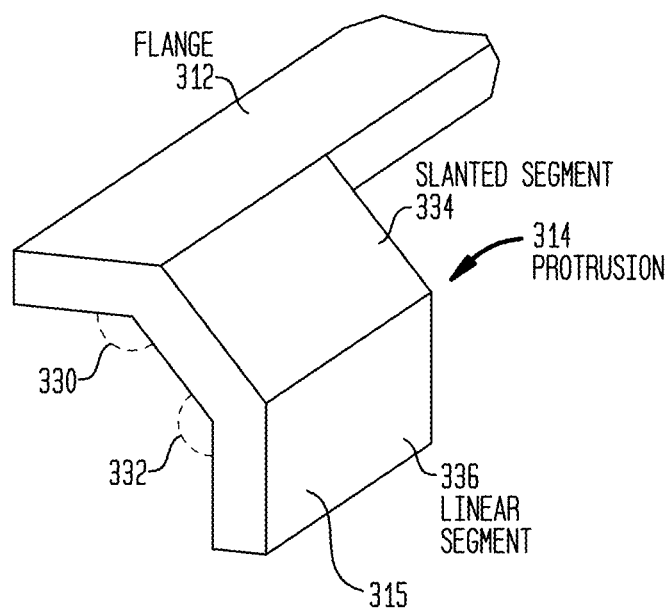
FIG. 3C is an alternative perspective view of a portion of the braze washer of FIG. 3B.

A problem that occurs during brazing is known as "flooding" where the melting braze material disperses (potentially) in an uncontrolled manner. During flooding, the braze material may, for example, flow onto the surface of the insulator and make contact with the conductors so as to compromise the function of the feedthrough. As such, in the embodiments of FIGS. 3A-3D, the protrusions 314 have a shape that is configured to reduce the detrimental affects of flooding by facilitating or encouraging the flow of braze material to a location between the insulator 304 and the housing sidewall 303. FIG. 3C is a perspective view of an exemplary protrusion 314 configured to encourage the flow of braze material between the insulator 304 and the housing sidewall 303.

More specifically, as shown in FIG. 3C, each of the protrusions 314 include a slanted segment 334 that extends from the flange 312 at an angle 330. The protrusions 314 also include a substantially linear segment 336 that extends from the distal end (i.e., the end not connected to the flange 312) of the slanted segment 334 at an angle 332. In general, the linear segment 336 is substantially perpendicular to the flange 312.

Figure 3D:
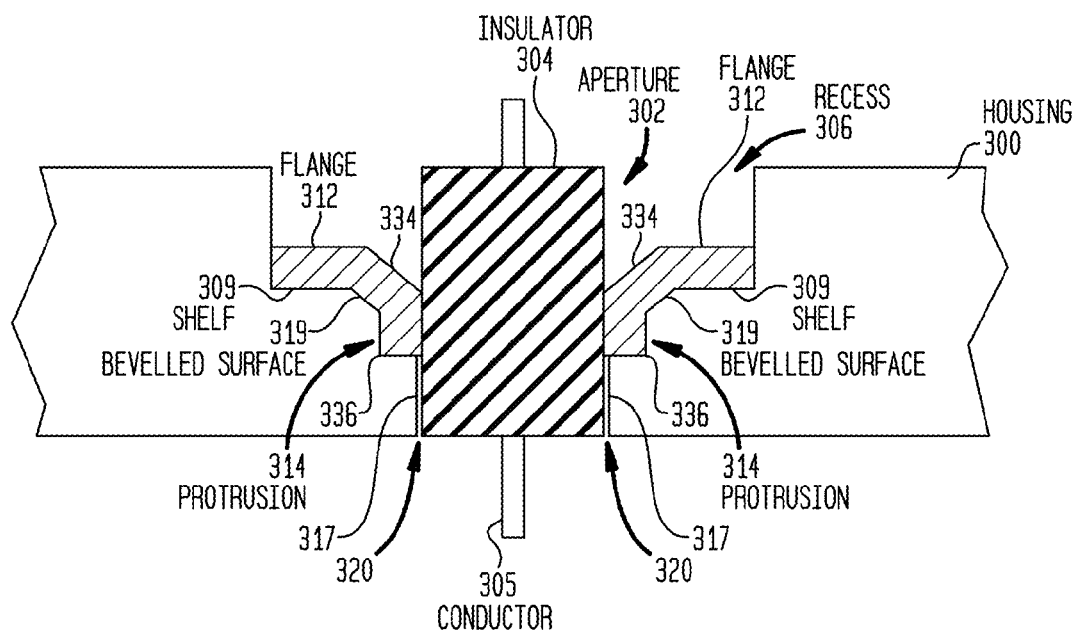
FIG. 3D is a cross-sectional view of the braze washer of FIG. 3B, the implantable housing of FIG. 3A, and an insulator in accordance with embodiments presented herein.

As shown in the cross-sectional view of FIG. 3D, the braze washer 310 is configured to be inserted into the aperture 302 and mate with the housing 300 (i.e., the flange 312 is configured to abut a surface of the housing 300). In the embodiments of FIG. 3D, the flange 312 abuts the shelf 309 created by recess 306. In alternative embodiments, the recess 306 may be omitted and the flange 312 may abut the outer surface 301 of the housing 300. Additionally, when the braze washer 310 is inserted into the aperture 302, braze protrusions 314 are positioned in the indentations 308 such that the slanted segment 334 rests against a beveled surface 319 of the indentations 308.

Outer surfaces 315 of the linear segments 336 of the braze protrusions 314 may be substantially aligned with (i.e., substantially even with) surfaces 317 of the housing sidewall 303 between indentations 308. Alternatively, the outer surfaces 315 of the linear segments 336 of the braze protrusions 314 may extend further into the aperture 302 than the surfaces 317 of the housing sidewall 303.

As shown, the insulator 304 is configured to substantially fill the aperture 302 so as to be in close proximity to the surfaces 317 of the housing sidewall 303 and the surfaces 315 of the braze protrusions 314. In general, a small gap 320 will be present between the insulator 304 and surfaces 317. As shown in FIG. 3D, the insulator 304 may be in contact with surfaces 315 of protrusions 314. Alternatively, the insulator 304 may be spaced from the surfaces 315 by a gap that is the same or different width as gap 320. In summary, when the insulator 304 is inserted into the aperture 302, the braze protrusions 314 will be positioned between the insulator 304 and the housing sidewall 303.

When the braze washer 310 and insulator 304 are positioned in housing 300, heat is applied to melt the braze washer 310. Because the protrusions 314 of the braze washer 310 are positioned between the insulator 304 and the housing sidewall 303 (i.e., the close-fitting parts), the embodiments of FIGS. 3A-3D do not rely solely on capillary action to position braze material between the close-fitting parts (the insulator 304 and the housing sidewall 303).

In summary, the embodiments of FIGS. 3A-3D locate a small amount of braze material within the aperture 302 (i.e., the protrusions 314 between the housing 300 and the insulator 304) supplemented by additional material adjacent to the aperture (flange 312). This arrangement provides for optimum heat transfer between the braze material and the close-fitting parts, thereby leading to efficient wetting. In these embodiments, the resulting braze joint has only localized (discrete) enlargements of the joint (i.e., enlargements at the protrusions/indentations) so as to retain strength advantages of a narrow joint.

In the embodiments of FIG. 3D, braze washer 310 and/or housing 300 are designed such that the insulator 304 is press-fit into the aperture 302 and the braze washer 310. That is, the protrusions 314 provide a small amount of resistance to the insulator 304 during insertion so as to retain the insulator 304 within the aperture prior to brazing and joining to the housing 300. More specifically, as noted above, the protrusions 314 are sized such that the surfaces 315 of the braze protrusions 314 extend into the aperture 302 beyond the surfaces 317 so as to make contact with the insulator 304 as it is inserted into the aperture. In other embodiments, the linear segments 336 of the protrusions 314 are oriented (e.g., tilted) so as extend into the aperture 302 as to make contact with the insulator 304 as it is inserted into the aperture. In alternative embodiments, the insulator 304 rests on a lip (not shown) of housing 300 during the brazing process.

Figure 4A:
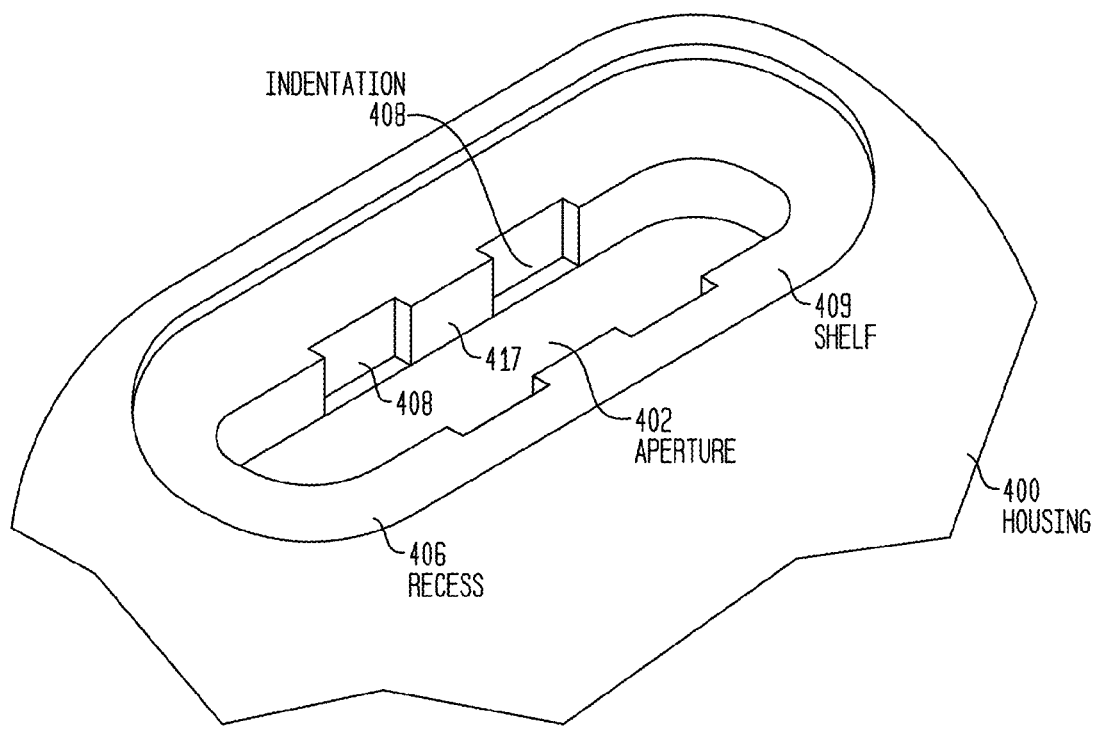
FIG. 4A is a perspective view of a portion of an implantable housing in accordance with embodiments presented herein.

FIG. 4A is a perspective view of a portion of an implantable housing 400 of an implantable medical device in accordance with further embodiments presented herein. The housing 400 includes an elongate aperture 402 that extends through the housing 400. The aperture 402 is substantially surrounded by a housing sidewall 403. The housing 400 also includes a plurality of indentations 408 that extend into the housing sidewall 403 from the aperture 402. As such, the indentations 408 are disposed around the aperture 402. In the embodiments of FIG. 4A, the housing 400 also includes an elongate recess 406 that forms a shelf 409 around a portion of the aperture 402.

The aperture 402 is configured to receive an insulator 404 (FIG. 4C) that includes a plurality of conductors 405 (FIG. 4C) extending therethrough. In order to ensure that the housing 400 provides a hermetic seal between electrical components inside the housing 400 and the recipient's tissue and bodily fluid, the insulator 404 is joined to the housing through brazing. That is, insulator 404 is configured to be positioned in the aperture 402 such that braze material flows between the insulator 404 and the housing 400. When the braze material cools and hardens, the insulator 404 is hermetically joined to the housing 400.

In order to perform the brazing, the braze material is first positioned in proximity to the insulator 404 and the housing 400. In accordance with certain embodiments presented herein, the braze material is in the form of a braze washer. FIG. 4B is a perspective view of an exemplary braze washer 410. As shown, the braze washer 410 includes an elongate top flange 412 and a plurality of first protrusions 414 that extend from the flange in a first direction. In the embodiments of FIG. 4B, the braze washer 410 also includes a plurality of second braze protrusions 444 that extend in a substantially opposing direction from the first braze protrusions 414.

As shown in the cross-sectional view of FIG. 4C, the braze washer 410 is configured to be inserted into the aperture 402 and mate with the surface of the housing 400 surrounding the aperture 402 (i.e., the flange 412 is configured to abut a surface of the housing 400). In the embodiments of FIG. 4C, the flange 412 abuts the shelf 409 created by recess 406. In alternative embodiments, the recess 406 may be omitted and the flange 412 may abut the outer surface of the housing 400. Additionally, when the braze washer 410 is inserted into the aperture 402, the first braze protrusions 414 are positioned in the indentations 408. The second braze protrusions 444 generally extend away from the housing 400 (i.e., in the opposite direction of the indentations 408).

Outer surfaces 415 of the braze protrusions 414 may be substantially aligned with (i.e., substantially even with) the surfaces 417 of the housing sidewall 403 between indentations 408. Alternatively, the outer surfaces 415 of the braze protrusions 414 may extend further into the aperture 402 than the surfaces 417.

As shown, the insulator 404 is configured to substantially fill the aperture 402 so as to be in close proximity to the surfaces 417 of the housing sidewall 403 and the surfaces 415 of the first braze protrusions 414. In general, a small gap 420 will be present between the insulator 404 and surfaces 417. As shown in FIG. 4C, the insulator 404 may be in contact with surfaces 415 of the first protrusions 414. Alternatively, the insulator 404 may be spaced from the protrusions by a gap that is the same or different width as gap 420. In summary, when the insulator 404 is inserted into the aperture 402, the braze protrusions 414 will be positioned between the insulator 404 and the housing sidewall 403.

When the braze washer 410 and insulator 404 are positioned in housing 400, heat is applied to melt the braze washer 410. Because the protrusions 414 of the braze washer 410 are positioned between the insulator 404 and the housing sidewall 403 (i.e., the close-fitting parts), the embodiments of FIGS. 4A-4C do not rely solely on capillary action to position braze material between the close-fitting parts (the insulator 404 and the housing sidewall 403).

To ensure the integrity of the braze joint, it may be beneficial that braze material flows along the insulator in a direction that is away from the gap 420 between the housing 400 and the insulator 404. The second protrusions 444 facilitate the flow of braze material away from the gap 420.

In summary, the embodiments of FIGS. 4A-4C locate a small amount of braze material within the aperture 402 (i.e., the first protrusions 414 between the housing 400 and the insulator 404) supplemented by additional material adjacent to the aperture (flange 412) as well as braze material extending away from the aperture 402 (i.e., second protrusions 444). This arrangement provides for optimum heat transfer between the braze material and the close-fitting parts, thereby leading to efficient wetting. In these embodiments, the resulting braze joint has only localized (discrete) enlargements of the gap (i.e., enlargements at the protrusions/indentations) so as to retain strength advantages of a narrow gap joint.

In the embodiments of FIG. 4C, braze washer 410 and/or housing 400 are designed such that the insulator 404 is press-fit into the aperture 402 and the braze washer 410. That is, the first braze protrusions 414 provide a small amount of resistance to the insulator 404 during insertion so as to retain the insulator 404 within the aperture prior to brazing and joining to the housing 400. More specifically, as noted above, the first braze protrusions 414 are sized such that the surfaces 415 extend into the aperture 402 beyond the surfaces 417 so as to make contact with the insulator 404 as it is inserted into the aperture. In other embodiments, the protrusions 414 are oriented (e.g., tilted) so as extend into the aperture 402 as to make contact with the insulator 404 as it is inserted into the aperture. In alternative embodiments, the insulator 404 rests on a lip (not shown) of housing 400 during the brazing process.

Figure 5A:
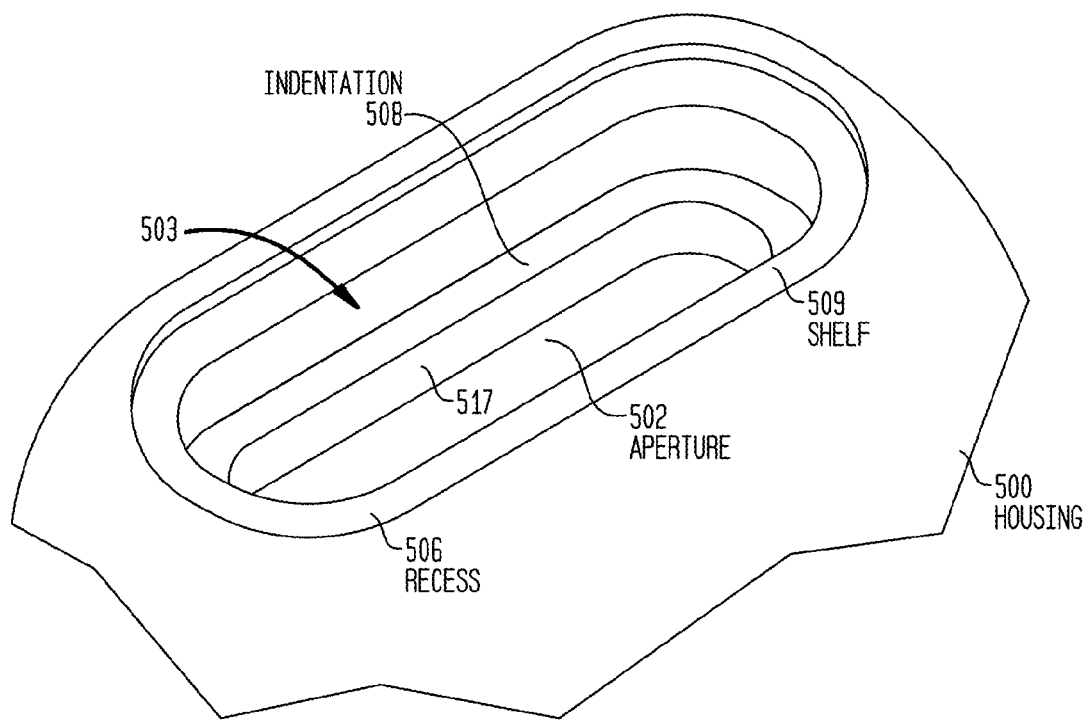
FIG. 5A is a perspective view of a portion of an implantable housing in accordance with embodiments presented herein.

FIG. 5A is a perspective view of a portion of an implantable housing 500 of an implantable medical device in accordance with other embodiments presented herein. The housing 500 includes an elongate aperture 502 that extends through the housing 500 and which is surrounded by a housing sidewall 503. The housing 500 also includes an indentation 508 that extends into the housing sidewall 503 from the aperture 502 so as to substantially surround a proximal portion of the aperture 502 (i.e., the indentation substantially surrounds a portion of the aperture 502 closest to the outer surface of the housing 500). In the embodiments of FIG. 5A, the housing 500 also includes an elongate recess 506 that forms a shelf 509 around the proximal end of the aperture 502.

The aperture 502 is configured to receive an insulator 504 (FIG. 5C) that includes a plurality of conductors 505 (FIG. 5C) extending therethrough. In order to ensure that the housing 500 provides a hermetic seal between electrical components inside the housing 500 and the recipient's tissue and bodily fluid, the insulator 504 is joined to the housing through brazing. That is, insulator 504 is configured to be positioned in the aperture 502 such that braze material flows between the insulator 504 and the housing sidewall 503. When the braze material cools and hardens, the insulator 504 is hermetically joined to the housing 500.

In order to perform the brazing, the braze material is first positioned in proximity to the insulator 504 and the housing 500. In accordance with certain embodiments presented herein, the braze material is in the form of a braze washer. FIG. 5B is a perspective view of an exemplary braze washer 510. As shown, the braze washer 510 includes an elongate top flange 512 and a single protrusion 514 that extend from the flange in a first direction. The single protrusions 514 is sometimes referred to herein as a continuous protrusion or lip 514 that extends around the circumference of the aperture 502 (i.e., surrounds the aperture 502).

As shown in the cross-sectional view of FIG. 5C, the braze washer 510 is configured to be inserted into the aperture 502 and mate with housing 500 (i.e., the flange 512 is configured to abut a surface of the housing 500). In the embodiments of FIG. 5C, the flange 512 abuts the shelf 509 created by recess 506. In alternative embodiments, the recess 506 may be omitted and the flange 512 may abut the outer surface of the housing 500. Additionally, when the braze washer 510 is inserted into the aperture 502, the braze protrusion 514 is positioned in the indentation 508 so as to substantially fill the indentation 508 and substantially surround the proximal portion of the aperture 502.

Outer surface 515 of the braze protrusion 514 may be substantially aligned with (i.e., substantially even with) the surface 517 of the housing sidewall 503 between the indentation 508 and a distal end of the aperture 502 (i.e., the surface of the housing that surrounds a portion of the aperture 502 closest to the inner surface of the housing 500). Alternatively, the outer surface 515 of the braze protrusions 514 may extend further into the aperture 502 than the surface 517 of the housing sidewall 503.

As shown, the insulator 504 is configured to substantially fill the aperture 502 so as to be in close proximity to the surface 517 of the housing sidewall 503 and the surface 515 of the braze protrusion 514. In general, a small gap 520 will be present between the insulator 504 and surface 517. As shown in FIG. 5C, the insulator 504 may be in contact with surface 515 of protrusion 514. Alternatively, the insulator 504 may be spaced from the protrusion 514 by a gap that is the same or different width as gap 520. In summary, when the insulator 504 is inserted into the aperture 502, the braze protrusion 514 will be positioned between the insulator 504 and the housing sidewall 503.

When the braze washer 510 and insulator 504 are positioned in housing 500, heat is applied to melt the braze washer 510. Because the protrusion 514 of the braze washer 510 is positioned between the insulator 504 and the housing sidewall 503 (i.e., the close-fitting parts), the embodiments of FIGS. 5A-5C do not rely solely on capillary action to position braze material between the close-fitting parts (the insulator 504 and the housing sidewall 503).

In summary, the embodiments of FIGS. 5A-5C locate a small amount of braze material within the aperture 502 (i.e., the protrusions 514 between the housing 500 and the insulator 504) supplemented by additional material adjacent to the aperture (flange 512). This arrangement provides for optimum heat transfer between the braze material and the close-fitting parts, thereby leading to efficient wetting.

In the embodiments of FIG. 5C, braze washer 510 and/or housing 500 are designed such that the insulator 504 is press-fit into the aperture 502 and the braze washer 510. That is, the protrusion 514 provides a small amount of resistance to the insulator 504 during insertion so as to retain the insulator 504 within the aperture prior to brazing and joining to the housing 500. More specifically, as noted above, the protrusion 514 is sized such that the surface 515 extends into the aperture 502 beyond the surfaces 517 so as to make contact with the insulator 504 as it is inserted into the aperture. In other embodiments, the protrusion 514 is oriented (tilted) so as extend into the aperture 502 as to make contact with the insulator 504 as it is inserted into the aperture. In alternative embodiments, the insulator 504 rests on a lip (not shown) of housing 500 during the brazing process.

Figure 6:
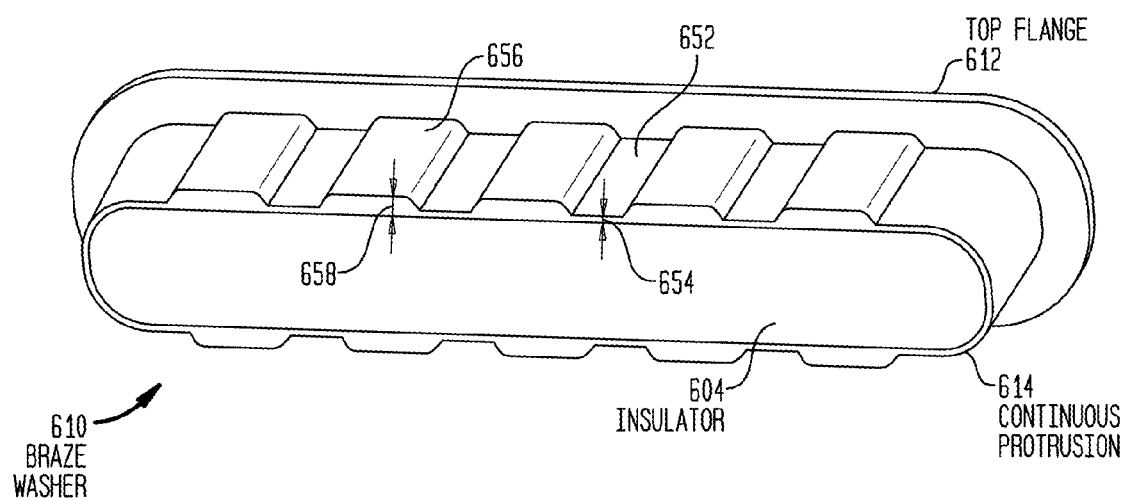
FIG. 6 is a perspective view of a braze washer of and an insulator in accordance with embodiments presented herein.

It is to be appreciated that the embodiments described above with reference to FIGS. 2A-5C are not mutually exclusive and may be combined in various combinations. For example, FIG. 6 illustrates an embodiment that combines a relatively thin continuous protrusion of FIGS. 5B and 5C with thicker discrete protrusions of FIGS. 2B-2D. More specifically, FIG. 6 is a perspective view of a braze washer 610 that is disposed around an insulator 604. As shown, the braze washer 610 includes an elongate top flange 612 and a continuous protrusion 614 that extends from the flange in a first direction. The continuous protrusion 614 extends along an inner circumference of the flange 612 and has relatively thinner sections 652 and relatively thicker thickness 656.

In the embodiments of FIG. 6, the braze washer 610 is configured to mate with a housing that has an aperture and indentations that correspond to the continuous protrusion 614. That is, in such embodiments the housing includes a continuous indentation with thick areas and thin areas configured to receive the thick sections 656 and thin sections 652, respectively, of continuous protrusion 614.

The above embodiments have been primarily described with reference to the use of solid braze washers as the braze material. It is to be appreciated that other braze materials may be used instead of, or in conjunction with, a solid braze washer. For example, FIG. 7 illustrates an embodiment in which an insulator 705 is positioned in an aperture 702 of a housing 700. Indentations 708 extend into the housing sidewall 703 from the aperture 702. In the embodiments of FIG. 7, the braze material comprises braze paste 782 (i.e., a very thick viscous fluid). The braze paste 782 is positioned in the indentations 708. In another embodiment, braze paste 782 may be used in conjunction with a braze washer configured to be disposed adjacent to the surface 701 of the housing 700.

When the braze paste 782 is positioned in the indentations 708, heat is applied to fully melt the braze paste 782. Because the braze paste 782 is positioned between the insulator 704 and the housing sidewall 703 (i.e., the close-fitting parts), the embodiments of FIG. 7 do not rely solely on capillary action to position braze material between the close-fitting parts (the insulator 704 and the housing sidewall 703).

In summary, the embodiments of FIG. 7 locate a small amount of braze material within the aperture 702 (i.e., the braze paste 782 between the housing 700 and the insulator 704). This arrangement provides for optimum heat transfer between the braze material and the close-fitting parts, thereby leading to efficient wetting. In these embodiments, the resulting braze joint has only localized (discrete) enlargements of the joint (i.e., enlargements at the protrusions/indentations) so as to retain strength advantages of a narrow joint.

In certain examples, the braze paste 782 may be positioned in the indentations directly from the outer surface 701 through the aperture 702. However, in alternative embodiments, such as the embodiments of FIG. 7, the housing 700 may include through-holes 786 that extend from the outer surface 701 through the housing 700 to the indentations 708. These through-holes 786 provide an access path for deposition of the braze paste into the more indentations 708 that is separate from the aperture 702. Such through-holes may be useful, for example, when the indentations 708 are not directly accessible via the aperture 702 once the insulator 704 and/or a braze washer is positioned in or adjacent to the housing 700.

As noted, the above embodiments illustrate the use of indentations in a housing sidewall adjacent to an aperture. In general, the indentations function as a mechanism that enables the braze material to be positioned between an insulator and a housing prior to brazing. It is to be appreciated that such indentations may not necessarily be disposed in the housing, but rather may be disposed in the insulator. FIGS. 8A and 8B are perspective views of an insulator 804 and a housing 800, respectively, in accordance with one such embodiment.

More specifically, as shown in FIG. 8A the insulator 804 has an elongate shape defined by an outer wall 890. The insulator 804 also comprises a plurality of indentations 808 extending into the insulator 804 from the outer wall 890.

The insulator 804 is configured to be positioned in an aperture 802 of housing 800 of FIG. 8B. When positioned in the aperture 802, the outer wall 890 of insulator 804 is in close proximity to housing sidewall 803. Subsequently, braze material, such as, braze washer 310 (as described above with reference to FIGS. 3A-3D) or another braze washer may be positioned such that a portion of the braze material is disposed in the indentations 808 (i.e., between the insulator 808 and the housing sidewall 803).

In accordance with the above or other embodiments, the braze material may comprises a single unitary element or a multi-part element. For example, a braze washer may comprise protrusions that are integrated with a flange or a braze washer may comprise protrusions that are physically separate from the flange. Alternatively, a braze washer may comprise only a top flange and may be used with one or more discrete braze elements (e.g., braze beads) that are positioned in the indentations prior to brazing.

Additionally, FIGS. 2A-8 primarily illustrate the use of braze washers that have a contiguous structure that extend around an aperture in a housing (i.e., form a continuous ring-shape). It is to be appreciated that embodiments may include braze washers that do not extend around the entirely of an aperture. For example, embodiments may include two or more discrete sections that extend around only a portion (or the entirety) of an aperture (e.g., horseshoe-shaped washers rather than ring-shaped washers).

A feedthrough may be formed by joining an insulator (e.g., a ceramic insulator with wires extending therethrough) to a housing (e.g., a titanium housing) through the use of braze material. In certain conventional feedthroughs, the material combination has been an insulator formed from 96 percent (%) alumina that is joined to a Grade 2 titanium housing via TiCuNi 60 braze material. This and other material combinations are susceptible to weakening of the braze-ceramic bond as a result of nickel (Ni) and copper (Cu) diffusion. More specifically, Ni and Cu are strongly attracted by the titanium and are scavenged out of the braze joint, thereby weakening the joint.

Figure 9:
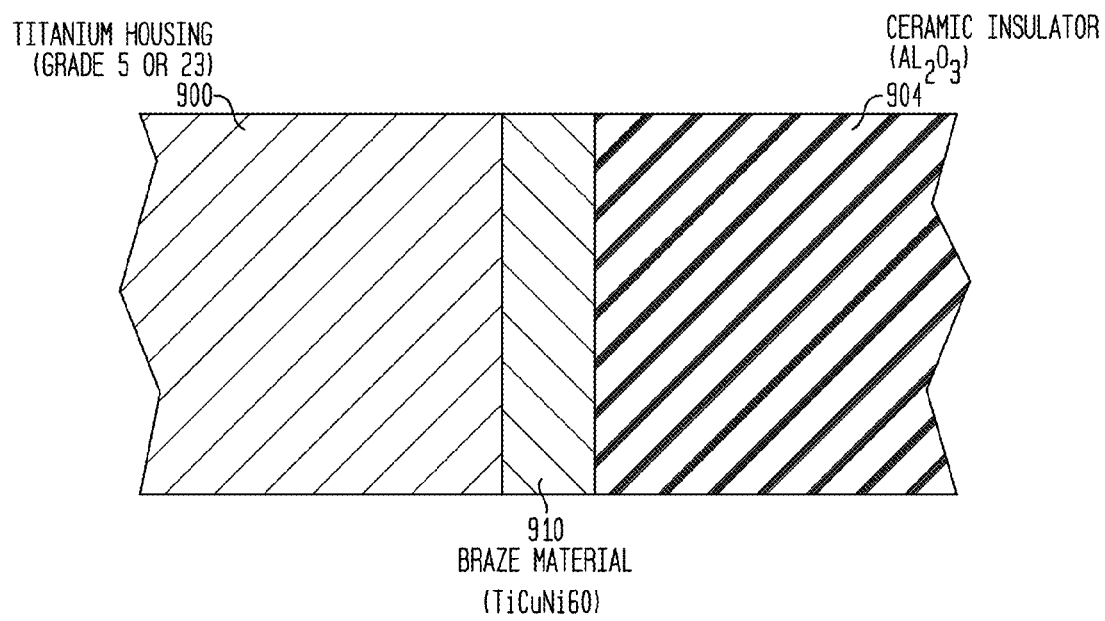
FIG. 9 is a schematic diagram of a braze joint in accordance with embodiments presented herein.

Certain embodiments presented herein are directed to new material combinations that reduce Ni and/or Cu diffusion following brazing, thereby improving the strength of the bond between an insulator and reactive braze material. FIG. 9 is a schematic diagram in which a diffusion restive titanium housing 900 (e.g., formed from a Grade 5 or Grade 23 titanium alloy) is joined to a ceramic insulator 904 (e.g., formed from $Al_2O_3$) via a reactive braze material 910 (e.g., TiCuNi 60). By using a housing 900 formed from a Grade 5 or Grade 23 titanium alloy (or another hard titanium alloy), the diffusion rate of the Ni and Cu into the titanium is significantly reduced and allows a wider process window in which to achieve a strong braze joint. A stronger braze joint results in a more reliable feedthrough, thereby reducing the risk of hermeticity failure.

Figure 10:
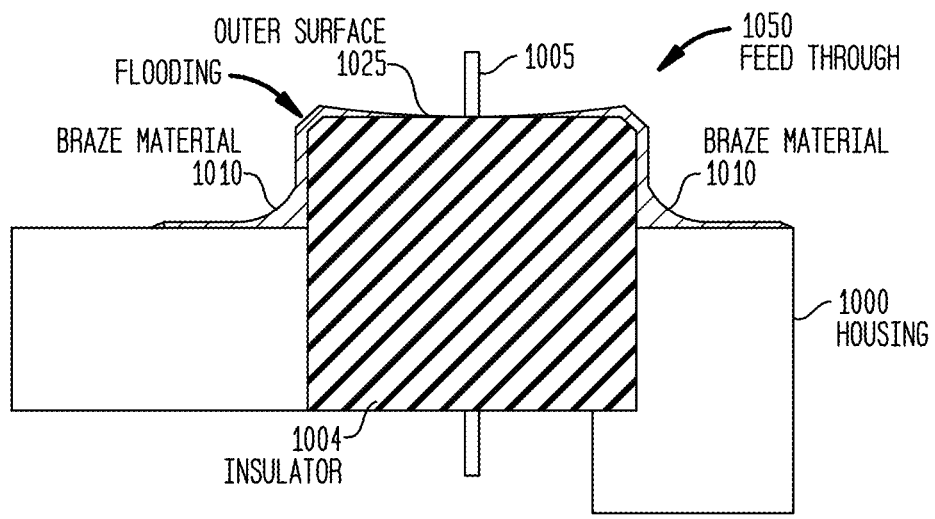
FIG. 10 is a cross-sectional view of a conventional feedthrough.

FIG. 10 is a cross-sectional view of a conventional feedthrough 1050 that comprises an insulator 1004 having one or more conductors 1005 extending therethrough. The insulator 1004 is positioned in a housing 1000 and joined to the housing via braze material 1010.

As noted above, braze materials used to join an insulator to a housing have an affinity to "wet" the surface of the insulator (i.e., spread over the surface in a thin layer). As shown in FIG. 10, when this braze flow is excessive, it can flow onto the outer surface 1025 of the insulator 1004 (i.e., the surface outside of the housing 1000 from which the conductors 1005 extend). This excessive flow is sometimes referred to as "flooding" and can compromise the function of the feedthrough by bringing braze material into close proximity to the conductors. Embodiments presented herein are directed to modifications to the feedthrough insulator in order to impede the flow of braze material onto the outer surface of the insulator.

Figure 11:
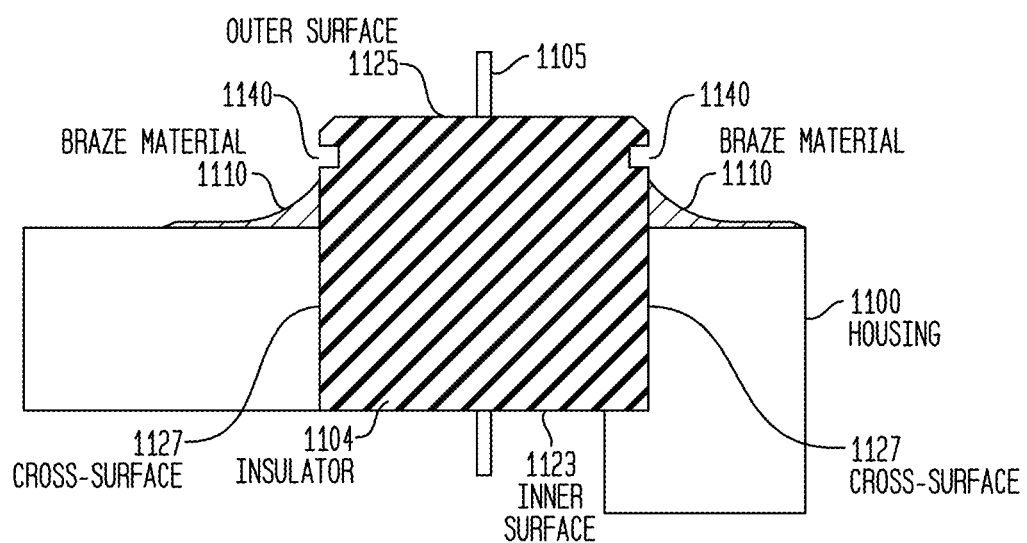
FIG. 11 is a cross-sectional view of a feedthrough in accordance with embodiments presented herein.

For example, FIG. 11 is a cross-sectional view of a feedthrough 1150 in accordance with such embodiments that includes one or more braze-impediment features. As shown, the feedthrough 1150 comprises an insulator 1104 and one or more conductors 1105 extending therethrough. The insulator 1104 has an inner surface 1123 (i.e., the surface inside the housing 1100 from which the conductors 1105 extend) and an outer surface 1125 (i.e., the surface outside of the housing 1100 from which the conductors 1105 extend). The surfaces 1123 and 1125 are connected by a substantially continuous outer wall or cross-surface 1127 extending around the outer edge of the insulator 1104.

As shown in FIG. 11, the cross-surface 1127 includes a thin notch or trough 1140 that extends around the cross-surface 1127 at a point between an initial location of the braze material 1110 and the outer surface 1125. In certain embodiments, the notch 1140 may be positioned in close proximity to the outer surface 1125. The notch 1140 has a width and/or depth so as to function as an impediment to the flow of the braze material 1110 towards the outer surface 1125, thereby preventing the braze material 1110 from interfering with the conductors 1105. As such, the notch 1140 is referred to herein as a braze-impediment feature.

Figure 12:
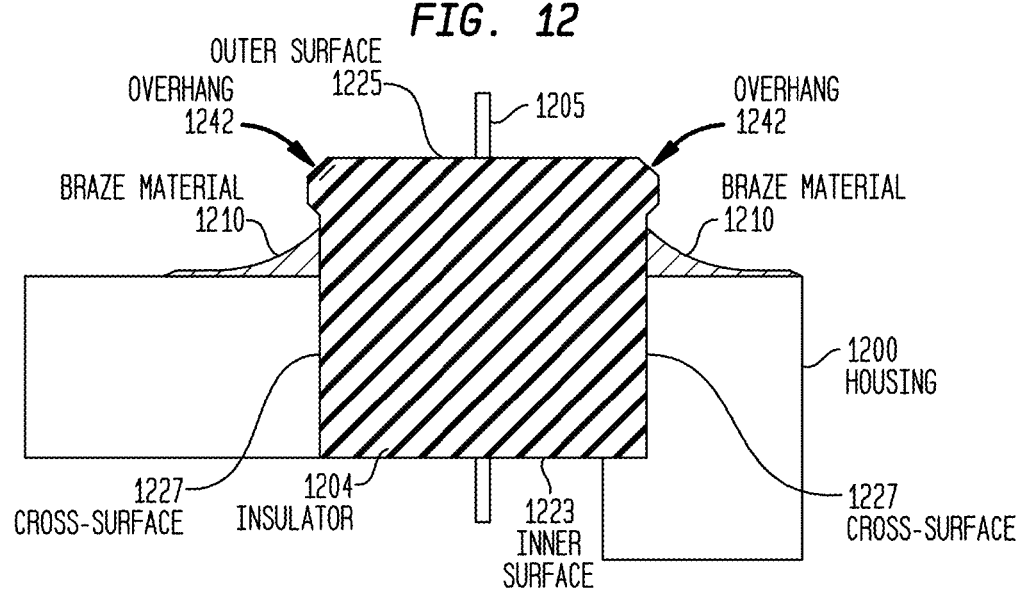
FIG. 12 is a cross-sectional view of a feedthrough in accordance with embodiments presented herein.

FIG. 12 is a cross-sectional view of a feedthrough 1250 in accordance with further embodiments presented herein. As shown, the feedthrough 1250 comprises an insulator 1204 one or more conductors 1205 extending therethrough. The insulator 1204 has an inner surface 1223 and an outer surface 1225. The surfaces 1223 and 1225 are connected by a substantially continuous cross-surface 1227 extending around the outer edge of the insulator 1204.

As shown in FIG. 12, the cross-surface 1227 includes an overhang 1242 that extends around the cross-surface 1227 at a point between an initial location of the braze material 1210 and the outer surface 1225. In certain embodiments, the overhang 1242 may be positioned in close proximity to the outer surface 1225. The overhang 1242 has a width and/or height so as to function as an impediment to the flow of the braze material 1210 towards the outer surface 1225, thereby preventing the braze material 1210 from interfering with the conductors 1205. As such, the overhang 1242 is referred to herein as a braze-impediment feature.

Figure 13:
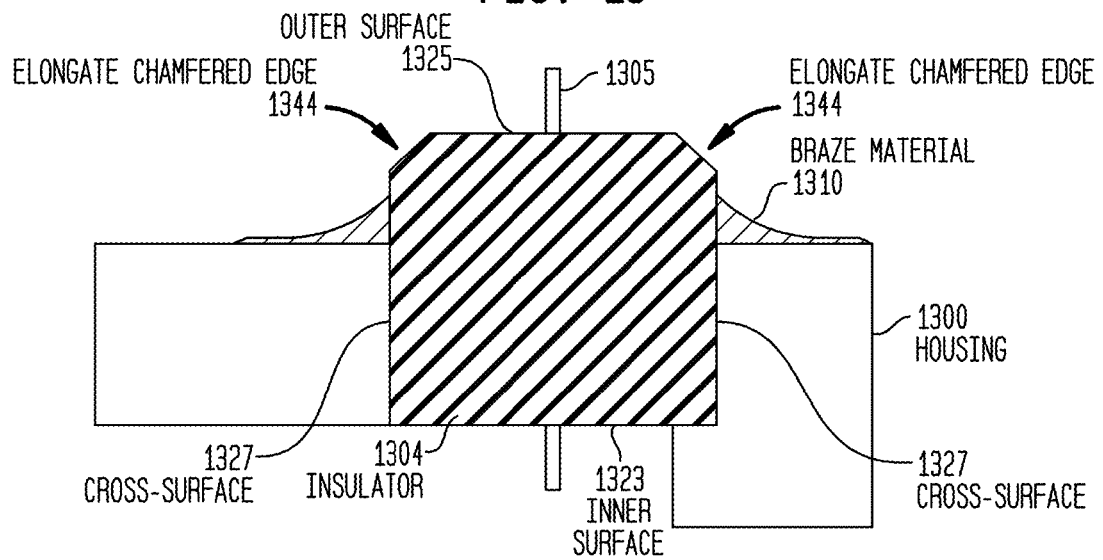
FIG. 13 is a cross-sectional view of a feedthrough in accordance with embodiments presented herein.

FIG. 13 is a cross-sectional view of a feedthrough 1350 in accordance with other embodiments presented herein. As shown, the feedthrough 1350 comprises an insulator 1304 one or more conductors 1305 extending therethrough. The insulator 1304 has an inner surface 1323 and an outer surface 1325. The surfaces 1323 and 1325 are connected by a substantially continuous cross-surface 1327 extending around the outer edge of the insulator 1304.

As shown in FIG. 13, the cross-surface 1327 is connected to the outer surface 1325 by an elongate chamfered edge 1344. The elongate chamfered edge 1344 has a length and/or pitch so as to function as an impediment to the flow of the braze material 1310 towards the outer surface 1325, thereby preventing the braze material 1310 from interfering with the conductors 1305. As such, the elongated chamfered edge 1344 is referred to herein as a braze-impediment feature.

FIGS. 11, 12, and 13 illustrate several embodiments in which the insulators include features configured to impede the flow of braze material. The braze-impediment features of FIGS. 11, 12 and 13 can be added to the insulator, for example, during a molding process used to form the insulator or added through a post-molding machining/cutting process. It is to be appreciated that the specific features of FIGS. 11, 12, and 13 are merely illustrative and that other features may be used in alternative embodiments.

Additionally, FIGS. 11, 12, and 13 illustrate embodiments in which the braze-impediment features are positioned so as to prevent the flow of braze material onto the outer surfaces of the insulators. In further embodiments, the same or different braze-impediment features may be positioned between an initial location of the braze material and the inner surfaces of the insulators so as to prevent the braze material 1310 from interfering with the conductors 1305 at the inner surfaces. In other words, braze-impediment features may also be positioned in close proximity to the inner surfaces of the insulators.

Figure 14C:
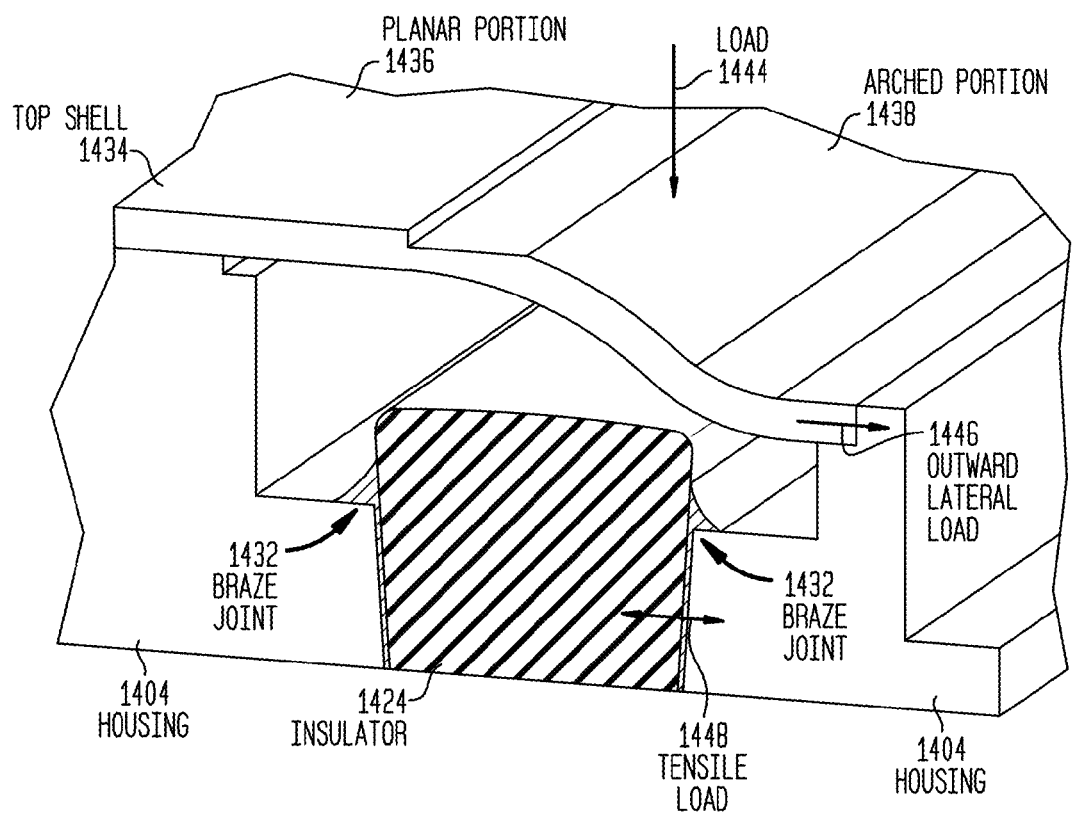
FIG. 14C is cross-sectional, perspective view of a portion of the implantable medical device of FIG. 14A.

As noted above, implantable medical devices include a feedthrough that is attached to a hermetically-sealed housing via one or more braze joints. In certain circumstances, the braze joints may be subject to tensile loading that has the potential to cause failure of the braze joints. For example, FIG. 14A is an exploded perspective view of a conventional implantable device 1400 that includes feedthroughs 1410A and 1410B that that may be subject to tensile loading in certain circumstances. FIG. 14B is a simplified cross-sectional view of a portion of the implantable device 1400, while FIG. 14C is a perspective view of a portion of the implantable medical device 1400.

Implantable device 1400 comprises a hermetically-sealed housing 1404 formed by an upper portion 1402A and a bottom portion 1402B. Housing 1404 defines a hermetic enclosure in which functional components 1412 are located. Functional components may include any mechanical, electrical, electro-mechanical and/or electronic components that are to be protected from a recipient's biological systems (e.g., tissue and bodily fluid). In the exemplary application of FIGS. 14A and 14B, functional components 1412 include a printed wiring board 1408 and a number of different electronic components 1428 mounted on the printed wiring board 1408.

Housing 1404 further comprises two elongate feedthroughs 1410A and 1410B disposed in apertures 1418A and 1418B, respectively, of housing 1404. The feedthroughs 1410A and 1410B each include a plurality of conductors 1405 disposed in an insulator 1424. The conductors 1405 facilitate the transfer of energy, data, materials, biological samples, etc. between functional components 1412 and the recipient, other implantable devices, of other elements outside of the hermetic housing 1404. As shown in FIG. 4B, the insulators 1424 are hermetically connected to the housing 1404 via braze joints 1432.

Due to the implant orientation and location, implantable device 1400 has a side, referred to herein as the impact side 1406, that is more likely to receive external forces applied to the device. That is, the surface of the implantable device which faces toward the skin of the recipient (when implanted) is likely to receive external forces, particularly when the device is implanted close to or immediately beneath the skin. It follows, then, that an opposing side of the device is generally facing toward the interior of the recipient and, as such, is less likely to directly receive external forces which may be applied to the device. As such, a protective top shell 1434 is connected to the housing 1404 to provide a degree of impact resistance to the implantable device 1400. The top shell 1434 and housing 1404 form a non-hermetic enclosure.

The conventional top shell 1414 comprises a planar portion 1436 defining a top surface of device 1400 and an arched portion 1438 extending from the planar portion 1436 to the housing 1404. As shown, a large section of the arched portion 1438 comprises an outward (upward) arch (i.e., arched away from the housing 1404). The end 1440 of the arched portion 1438 is configured to seat against a wall 1442 of the housing 1404.

As shown in FIG. 14B, a load 1444 may be placed on top shell 1436 at, for example, the arched portion 1438. Due to the outward arch shape of the arched portion 1438, the load 1444 acts to straighten out the arched portion 1438. As the arched portion 1438 starts to straighten, an outward lateral load 1446 is placed on the wall 1442 of the housing 1404. This outward lateral load 1446 on the housing in turn places a tensile load 1448 on the braze joint 1432 that connects the insulator 1424 to the housing 1404. That is, as the housing 1404 is pushed outward by the straightening of top shell 1434, the housing 1404 may pull away from the insulator 1424, thereby resulting in cracking and/or failure of the braze joint 1432. The tendency of the arched portion 1438 to straighten when a load 1444 is applied to planar portion 1426 is sometimes referred to herein as the "arch effect."

Embodiments presented herein are directed to reducing the arch effect and minimizing how much of a load that is applied to a top shell of an implantable medical device gets transmitted as a tensile load to a feedthrough and braze joint. In certain embodiments, an implantable medical device is configured such that a load applied to a top shell generates a compressive load on the feedthrough and braze joint, thereby inhibiting crack growth.

Figure 15:
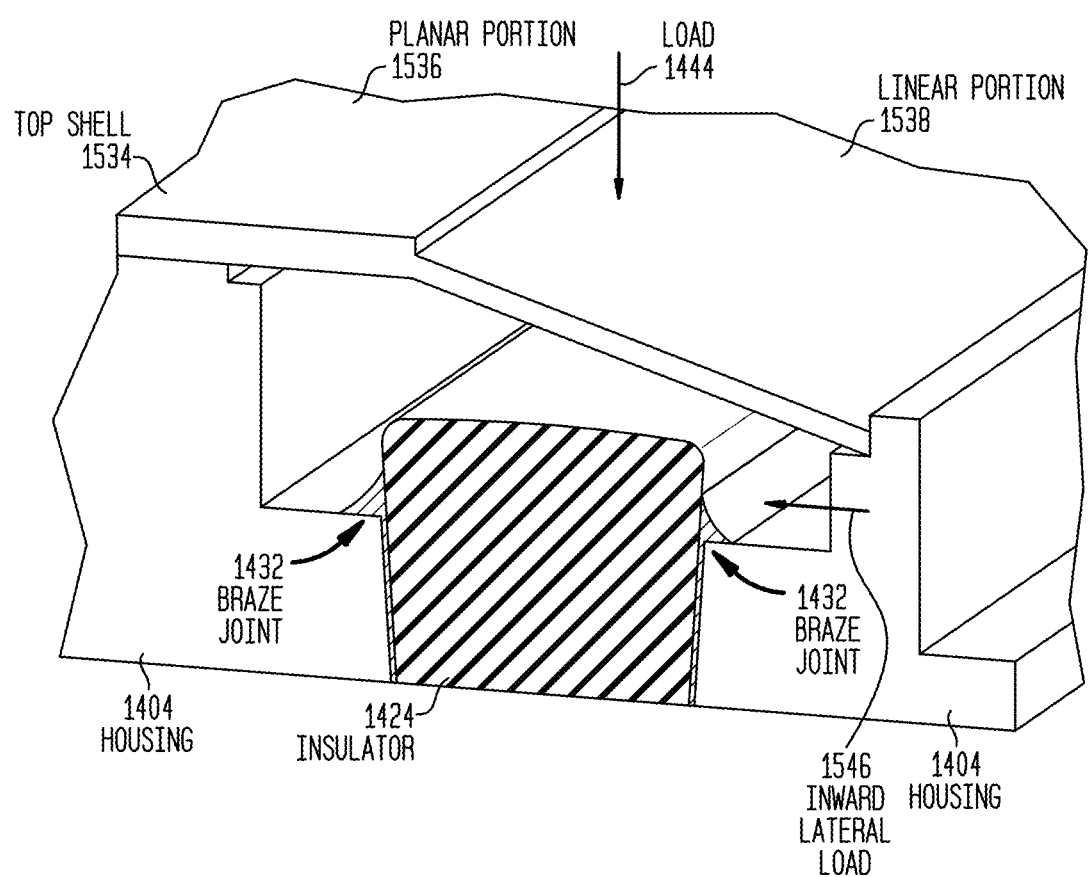
FIG. 15 is cross-sectional, perspective view of a portion of an implantable medical device in accordance with embodiments presented herein.

FIG. 15 illustrates one embodiment of an implantable medical device that includes a housing 1404 (as described above with reference to FIGS. 14A-14C) and a top shell 1534 configured to minimize tensile loading of the braze joint 1432 in response to an applied load 1444. The top shell 1534 includes a planar portion 1536 and a linear portion 1538 extending from the planar portion 1536 to the housing 1404. In the embodiments of FIG. 15, when load 1444 is applied, there is no tendency for any portion of the top shell to straighten (i.e., the linear portion 1538 is already straight), so less/reduced outward load (relative to conventional arrangements) is generated on the housing 1404. Because a reduced outward load is generated, a reduced or minimal tensile load is transmitted to the braze joint 1432.

In the embodiments of FIG. 15, not only is no outward later load generated, but the configuration of top shell 1524 has an added benefit that the top shell will tend to bend inwards (i.e., towards housing 1404) at planar portion 1536. The inward bending of planar portion 1536 may generate an inward lateral load 1546, which will cause compression of the braze joint 1432 so as to inhibit growth of cracks in the braze joint.

FIG. 15 illustrates the use of one linear segment to connect planar portion 1536 to housing 1404. In alternative embodiments, a series of connected linear segments may be used (e.g., a series of steps, a series of connected ramps, etc.)

Figure 16:
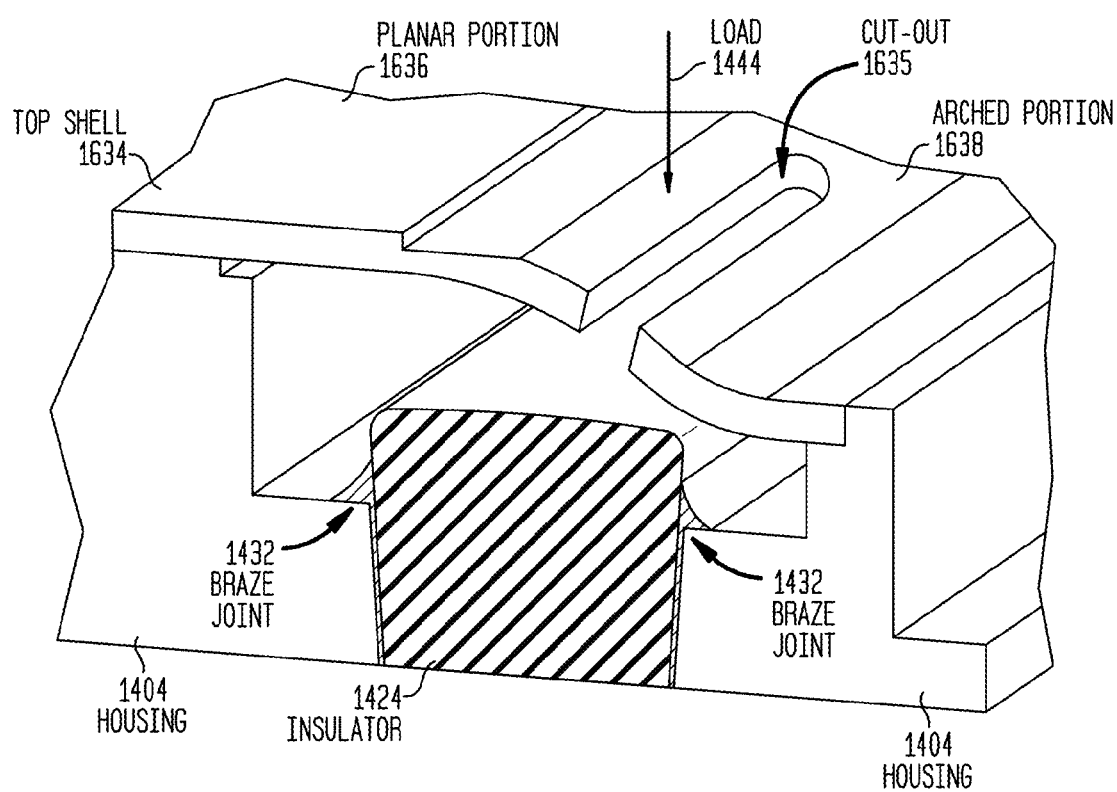
FIG. 16 is cross-sectional, perspective view of a portion of an implantable medical device in accordance with embodiments presented herein.

FIG. 16 illustrates an embodiment of an implantable medical device that includes a housing 1404 (as described above with reference to FIGS. 14A-14C) and a top shell 1634 configured to minimize tensile loading of the braze joint 1432 in response to an applied load 1444. The top shell 1634 includes a planar portion 1636 and an arched portion 1638 extending from the planar portion 1636 to the housing 1404. The arched portion 1636 comprises an outward (upward) arch (i.e., arched away from the housing 1404) and an elongate slot or cut-out 1635 in the arched portion 1638.

The cut-out 1635 functions to substantially mechanically decouple the end 1621 of the arched portion 1638 nearest to the planar portion 1636 from the end 1623 closest to the housing 1404. As a result of this mechanical decoupling of the two ends of the arched portion (due to the cut-out 1635), there is no tendency for the arched portion 1638 to straighten following application of load 1444. Because arched portion 1538 does not straight, a reduced outward load is generated on the housing 1404 and a reduced or minimal tensile load is transmitted to the braze joint 1432.

It is to be appreciated that the cut-out 1635 of FIG. 16 is merely illustrative. Cut-outs in accordance with other embodiments of the present invention may take a number of different shapes, sizes, locations, etc.

Figure 17:
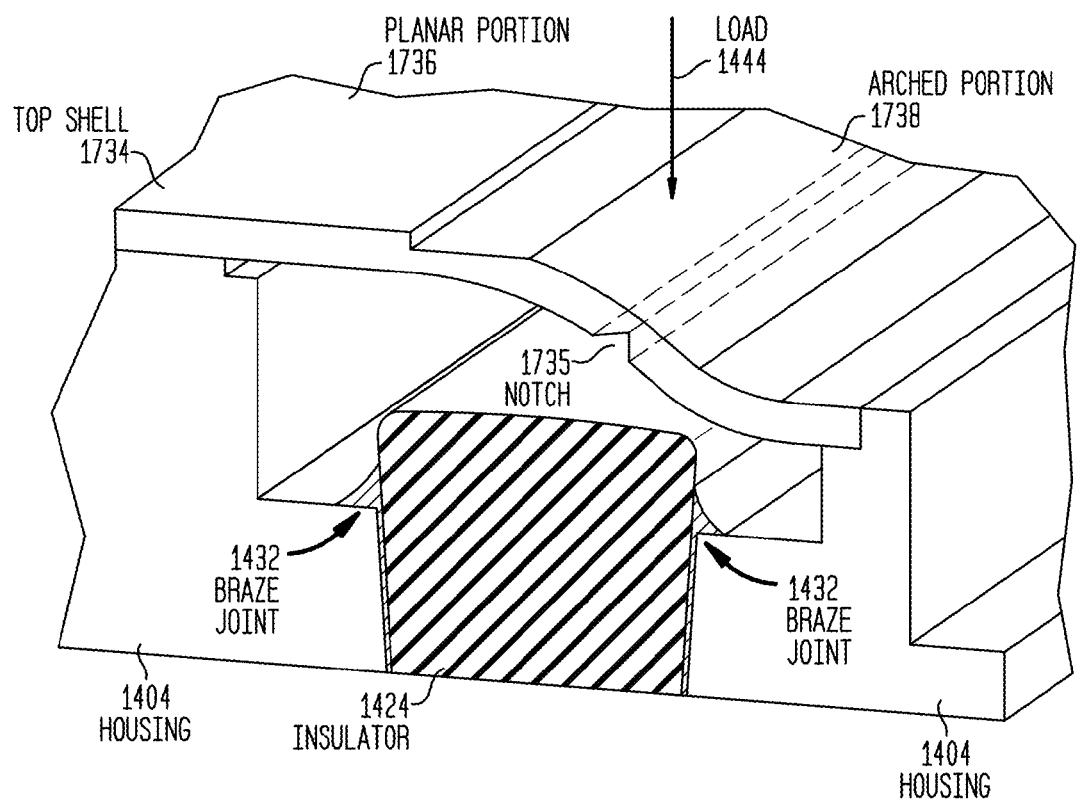
FIG. 17 is cross-sectional, perspective view of a portion of an implantable medical device in accordance with embodiments presented herein.

FIG. 17 illustrates an embodiment of an implantable medical device that includes a housing 1404 (as described above with reference to FIGS. 14A and 14B) and a top shell 1734 configured to minimize tensile loading of the braze joint 1432 in response to an applied load 1444. The top shell 1734 includes a planar portion 1736 and an arched portion 1738 extending from the planar portion 1736 to the housing 1404. The arched portion 1738 comprises an outward (upward) arch (i.e., arched away from the housing 1404) and a notch 1735. The notch 1735 is formed in the surface of the arched portion 1738 that is closest to the insulator 1424.

In the embodiments of FIG. 17, when load 1444 is applied, instead of attempting to straighten, the arched portion 1738 will buckle or deform inward at the notch 1735. As such, a reduced outward load is generated on the housing 1404 and a reduced or minimal tensile load is transmitted to the braze joint 1432.

FIG. 17 illustrates an embodiment that includes a single notch 1735 that is located substantially in the middle of the arched portion 1738. It is to be appreciated that this embodiment is illustrate and that the notch 1735 may be positioned differently in other embodiments. For example, a notch may also be provided at the surface of the arched portion 1738 that is farthest from the insulator 1424 (i.e., the outer surface of the top shell 1734).

It is also to be appreciated that a plurality of notches may be used in further embodiments. In another embodiment, rather than using a notch, the entire arched portion 1738 may be made very thin so that any portion of the arched portion will buckle in response to a load 1444.

The tendency of the arched portion 1438 of FIGS. 14A-14C to straighten out and generate the outward lateral load 1446 in response to a load 1444 is an inherent property of an outward arch shape. As such, in certain embodiments the outward lateral load 1446 may be reduced or eliminated by changing the curve of the arched portion.

Figure 18A:
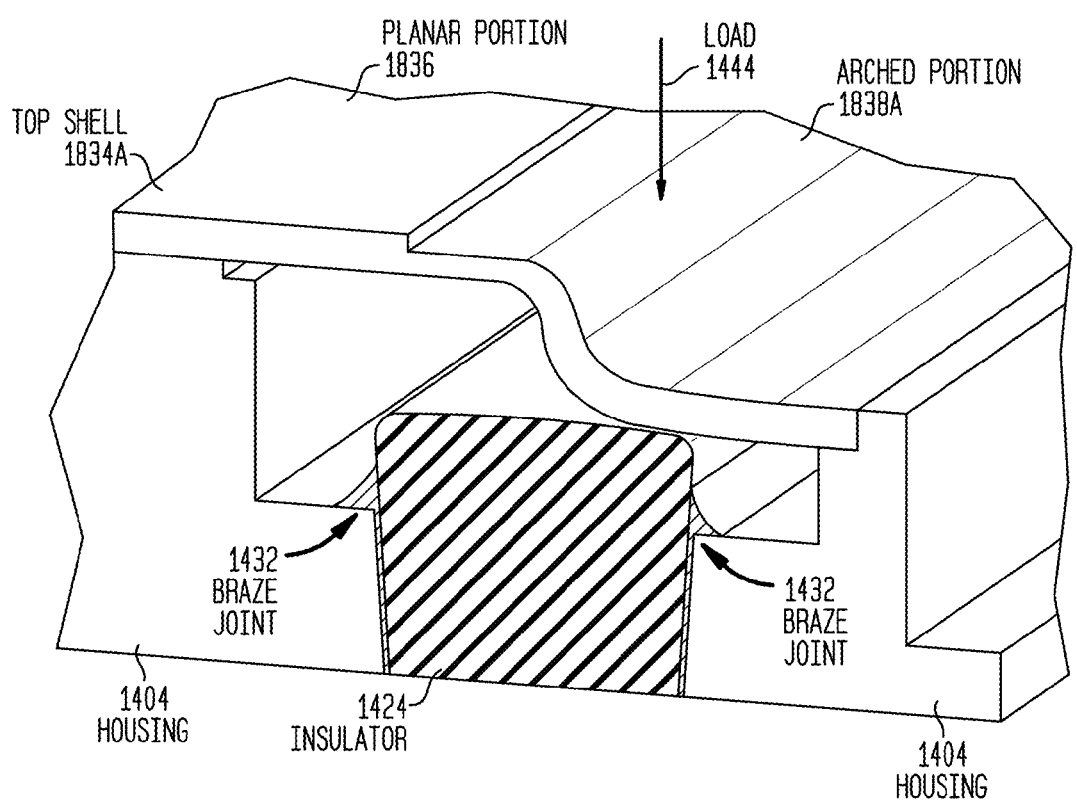
FIG. 18A is cross-sectional, perspective view of a portion of an implantable medical device in accordance with embodiments presented herein.

For example, FIG. 18A illustrates an embodiment of an implantable medical device that includes a housing 1404 (as described above with reference to FIGS. 14A and 14B) and a top shell 1834A configured to minimize tensile loading of the braze joint 1432 in response to an applied load 1444. The top shell 1834A includes a planar portion 1836 that and an arched portion 1838A extending from the planar portion 1836 to the housing 1404. The arched portion 1838A comprises an inward (downward) arch (i.e., arched towards the housing 1404) that does not have a tendency to straighten when load 1444 is applied and no outward load is generated on the housing 1404. Because no outward load is generated, no tensile load is transmitted to the braze joint 1432.

Figure 18B:
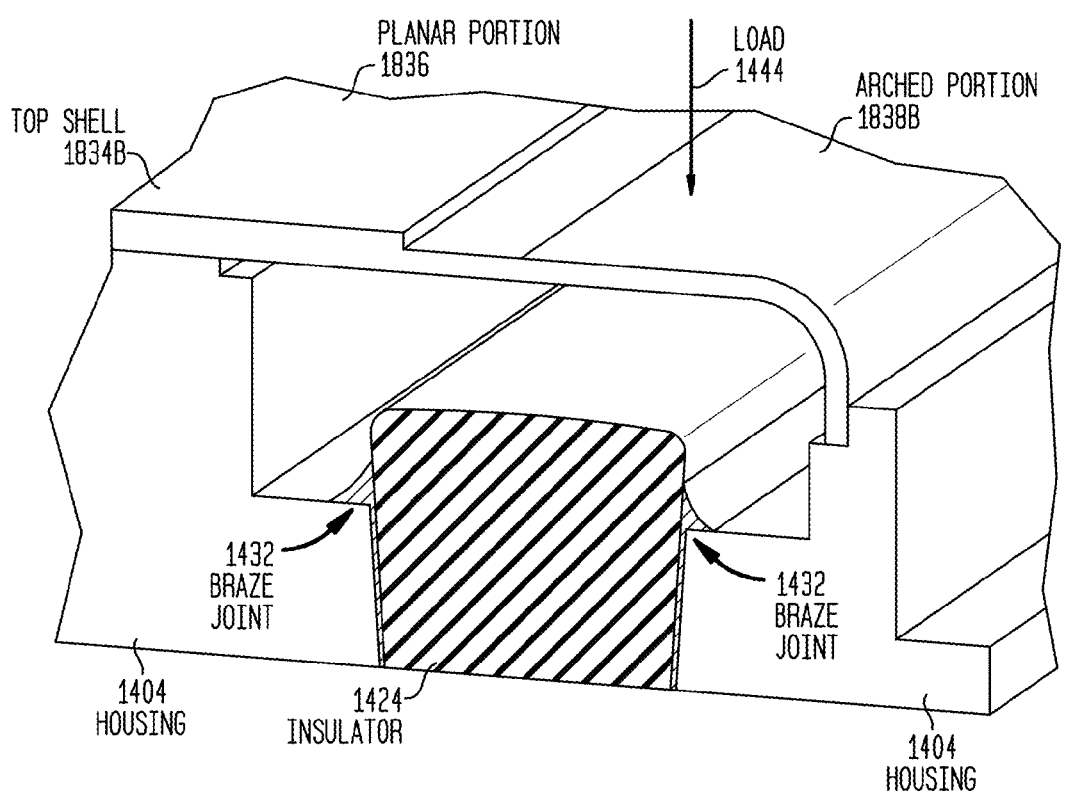
FIG. 18B is cross-sectional, perspective view of a portion of an implantable medical device in accordance with embodiments presented herein.

FIG. 18B illustrates further embodiments of a top shells 1834B having an alternative shaped arched portion 1838B. In these embodiments, the curve of the arched portion 1838B is changed so as to reduce or eliminate the tendency to straighten when a load is applied. It is to be appreciated that the curve of arched portion 1838B is illustrative and that arched portions having different curves may be used in alternative embodiments.

Figure 19A:
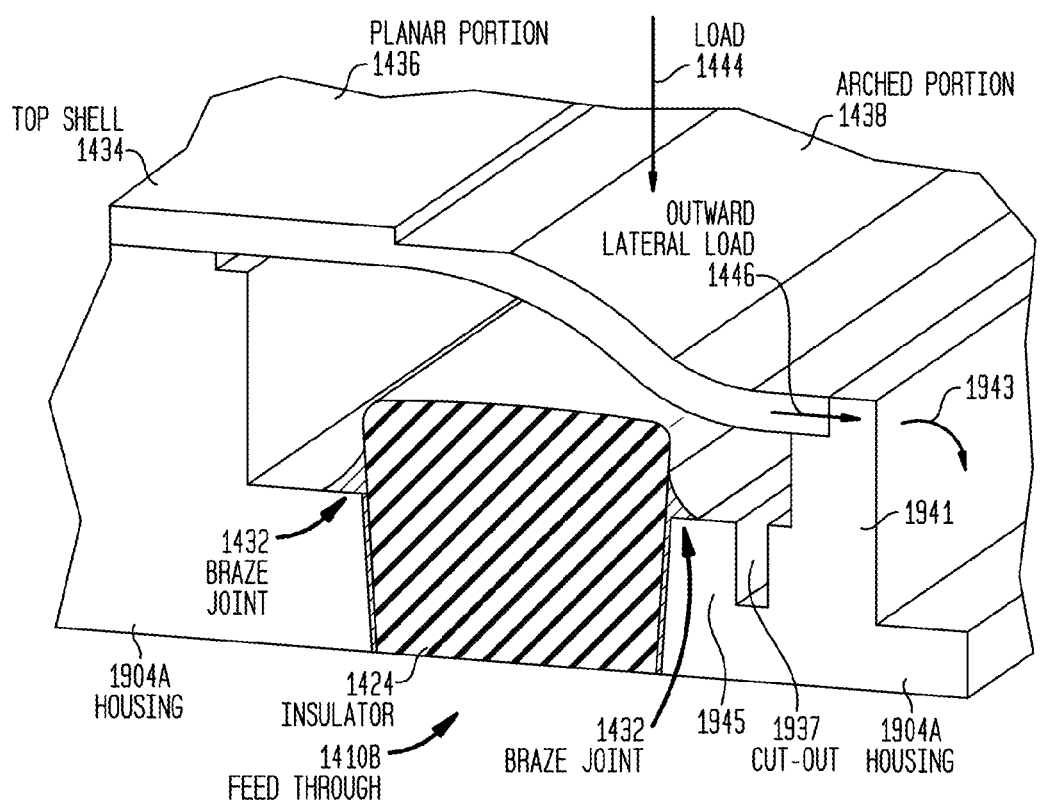
FIG. 19A is cross-sectional, perspective view of a portion of an implantable medical device in accordance with embodiments presented herein.

FIG. 19A illustrates an embodiment of an implantable medical device that includes a hermetically-sealed housing 1904A that is similar to housing 1404 (FIG. 14A). Two elongate feedthroughs 1410A and 1410B that comprise a plurality of conductors 1405 disposed in an insulator 1424 are positioned in housing 1904A. For ease of illustration, only the insulator 1424 of feedthrough 1410B is shown in FIG. 19A.

Attached to housing 1904A is a top shell 1434 as described above with reference to FIGS. 14A-14C. Similar to the arrangement of FIGS. 14A-14C, when a load 1444 is applied, arched portion 1438 places an outward lateral load 1446 on the housing 1904A. However, as shown in FIG. 19A, the housing 1904A includes a cut-out 1937 that is disposed between the portion 1941 of the housing 1904A that is subject to the outward lateral load 1446 and the braze joint 1432 that connects the insulator 1424 to the housing 1904. The cut-out 1937 functions to mechanically de-couple portion 1941 from a portion 1945 of the housing that is adjacent to the braze joint 1432 such that application of the outward lateral load 1446 to portion 1941 does not induce a tensile load on the braze joint 1432.

More specifically, as represented by arrow 1943 in FIG. 19A, the outward lateral load 1446 will push portion 1941 outward (i.e., away from the insulator 1424). Because of the cut-out 1937, the housing will bend or flex at the region adjacent to the cut-out 1937, thereby protecting the braze joint 1432 from tensile loading.

Figure 19B:
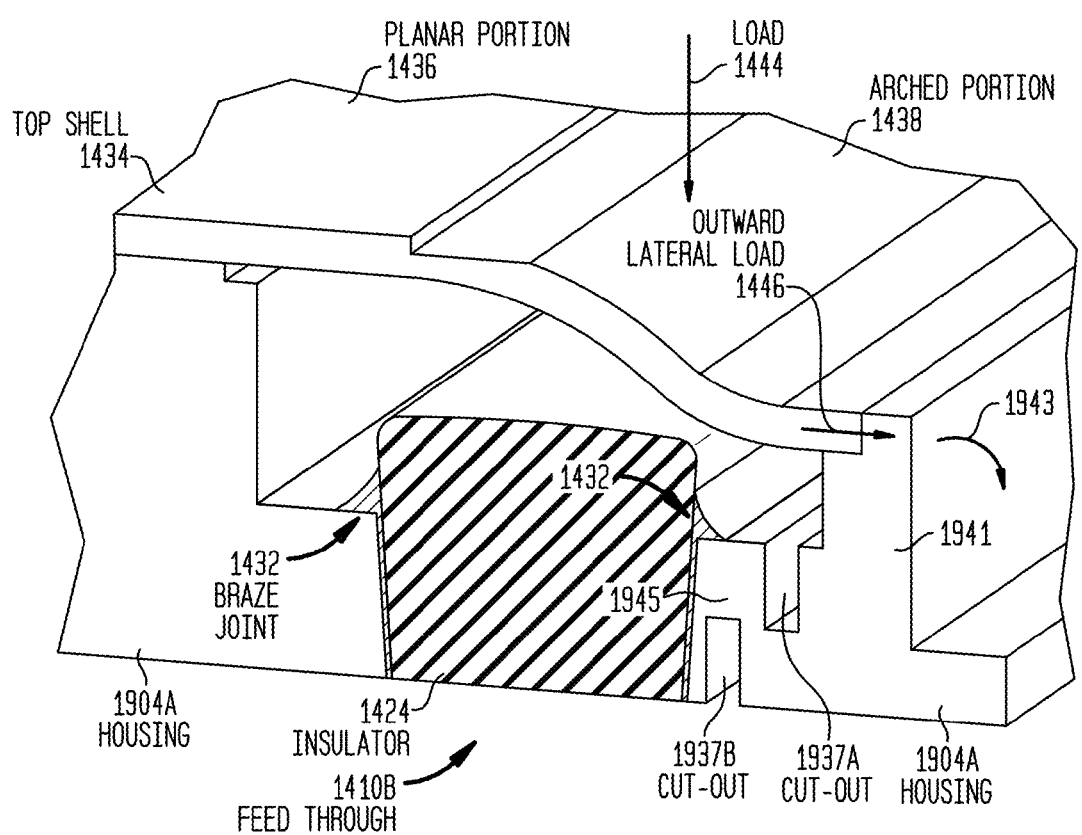
FIG. 19B is cross-sectional, perspective view of a portion of an implantable medical device in accordance with embodiments presented herein.

FIG. 19A illustrates an embodiment where a single cut-out 1937 is disposed between portions 1941 and 1945 of the housing 1904A. FIG. 19B illustrates an alternative embodiment where a housing 1904B includes two cut-outs 1951 and 1953 disposed between portions 1941 and 1945 of the housing 1904B. As shown, cut-out 1951 is an outward facing cut-out (i.e., facing top shell 1434), while cut-out 1953 is an inward facing cut-out (i.e., facing a lower portion of the housing).

Figure 19C:
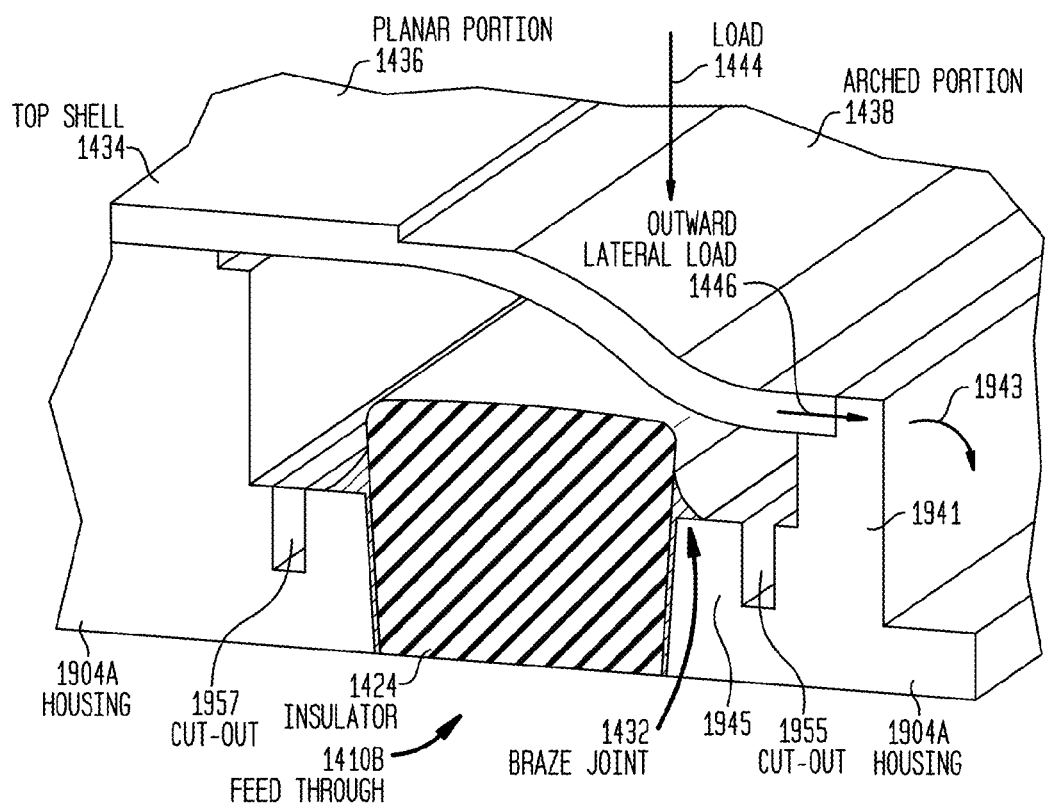
FIG. 19C is cross-sectional, perspective view of a portion of an implantable medical device in accordance with embodiments presented herein.

FIG. 19C illustrates a further embodiment where a housing 1904C includes two cut-outs 1955 and 1957. Cut-out 1955 is an outward facing cut-out that is disposed between portions 1941 and 1945 of the housing 1904B. Cut-out 1957 is also an outward facing cut-out, but is disposed on an opposing side of the feedthrough 1410B from cut-out 1955.

It is to be appreciated that the cut-out arrangements of FIGS. 19A-19C are illustrative and that various combinations of these embodiments and other cut-outs may be used in alternative embodiments. For example, multiple cut-outs may be disposed on each side of the feedthrough and these cut-outs may be any combination of outward facing cut-outs and/or inward facing cut-outs.

In the embodiments of FIGS. 19A-19C, not only is no tensile load applied to the braze joint 1432, but the use of the cut-outs have an added benefit that a portion of the housing may flex inwards (i.e., towards insulator 1424). This inward bending may cause compression of the braze joint 1432 so as to inhibit growth of cracks in the braze joint.

Figure 20:
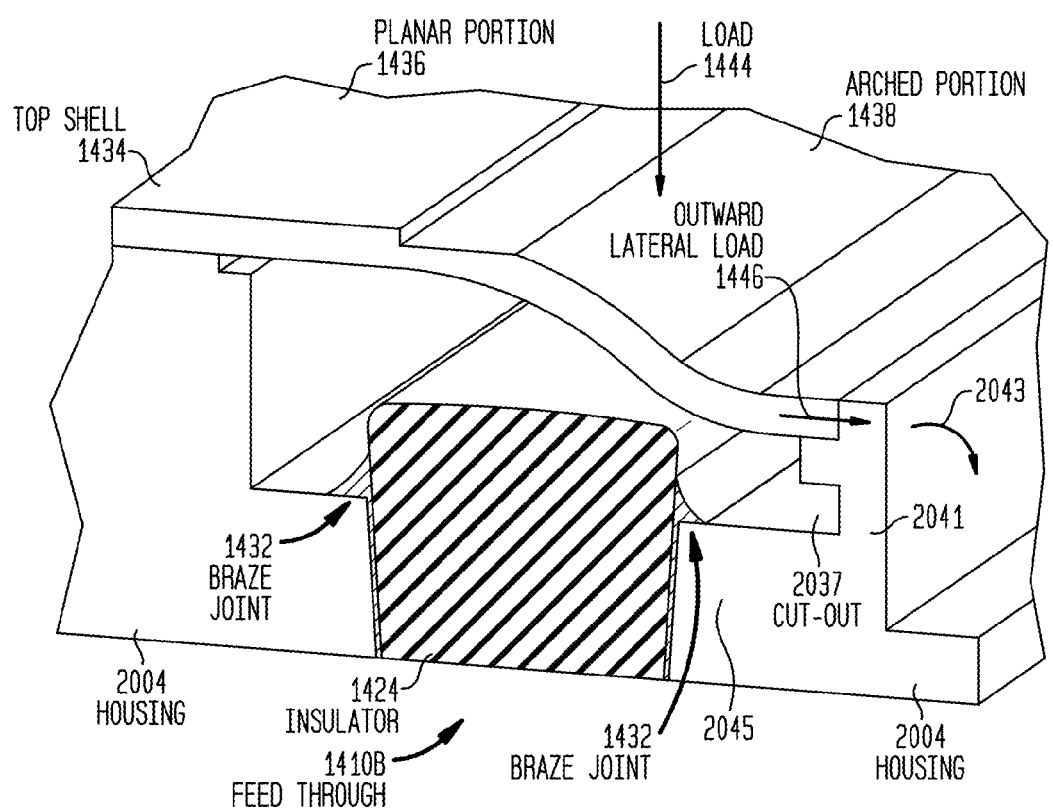
FIG. 20 is cross-sectional, perspective view of a portion of an implantable medical device in accordance with embodiments presented herein.

FIG. 20 illustrates an embodiment of an implantable medical device that includes a hermetically-sealed housing 2004 that is similar to housing 1404 (FIG. 14A). Housing 2004 further comprises two elongate feedthroughs 1410A and 1410B that comprise a plurality of conductors 1405 disposed in an insulator 1424. For ease of illustration, only the insulator 1424 of feedthrough 1410B is shown in FIG. 20.

Attached to housing 2004 is a top shell 1434 as described above with reference to FIGS. 14A-14C. Similar to the arrangement of FIGS. 14A-14C, when a load 1444 is applied, the arched portion 1438 places an outward lateral load 1446 on the housing 2004. However, as shown in FIG. 20, the housing 2004 includes a cut-out 2037 that is disposed between the portion 2041 of the housing 2004 that is subject to the outward lateral load 1446 and the braze joint 1432 that connects the insulator 1424 to the housing 2004. The cut-out 2037 functions to mechanically de-couple portion 2041 from the portion of the housing 2045 adjacent to the braze joint 1432 such that application of the outward lateral load 1446 to portion 2041 does not induce a tensile load on the braze joint 1432.

More specifically, as represented by arrow 2043 in FIG. 20, the outward lateral load 1446 will push portion 2041 outward (i.e., away from the insulator 1424). Because of the cut-out 2037, the housing will bend or flex at the region adjacent to the cut-out 2037, thereby protecting the braze joint 1432 from tensile loading.

In the embodiments of FIG. 20, not only is no tensile load applied to the braze joint 1432, but the use of the cut-out 2037 has an added benefit that the portion 2045 may flex inwards (i.e., towards insulator 1424). The inward bending of portion 2045 may cause compression of the braze joint 1432 so as to inhibit growth of cracks in the braze joint.

Figure 21:
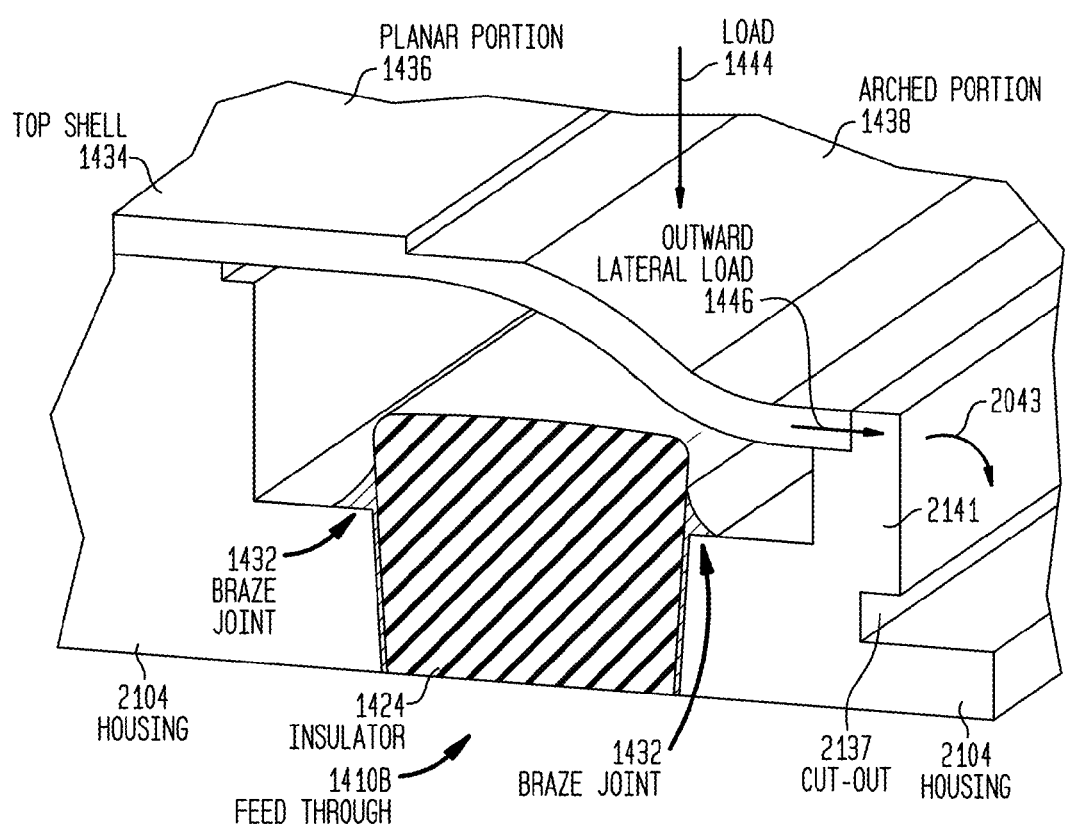
FIG. 21 is cross-sectional, perspective view of a portion of an implantable medical device in accordance with embodiments presented herein.

FIG. 21 illustrates an embodiment of an implantable medical device that includes a hermetically-sealed housing 2104 that is similar to housing 1404 (FIG. 14A). Housing 2104 further comprises two elongate feedthroughs 1410A and 1410B that comprise a plurality of conductors 1405 disposed in an insulator 1424. For ease of illustration, only the insulator 1424 of feedthrough 1410B is shown in FIG. 21.

Attached to housing 2104 is a top shell 1434 as described above with reference to FIGS. 14A-14C. Similar to the arrangement of FIGS. 14A-14C, when a load 1444 is applied, the arched portion 1438 places an outward lateral load 1446 on the housing 2104. However, as shown in FIG. 21, the housing 2104 includes a cut-out 2137 that is disposed between the portion 2141 of the housing 2104 that is subject to the outward lateral load 1446 and the braze joint 1432 that connects the insulator 1424 to the housing 2104. The cut-out 2137 functions to mechanically de-couple portion 2141 from the portion of the housing 2145 adjacent to the braze joint 1432 such that application of the outward lateral load 1446 to portion 2141 does not induce a tensile load on the braze joint 1432.

More specifically, as represented by arrow 2143 in FIG. 21, the outward lateral load 1446 will push portion 2141 outward (i.e., away from the insulator 1424). Because of the cut-out 2137, the housing will bend or flex at the region adjacent to the cut-out 2137, thereby protecting the braze joint 1432 from tensile loading.

In the embodiments of FIG. 21, not only is no tensile load applied to the braze joint 1432, but the use of the cut-out 2137 has an added benefit that the portion 2145 may flex inwards (i.e., towards insulator 1424). The inward bending of portion 2145 may cause compression of the braze joint 1432 so as to inhibit growth of cracks in the braze joint.

Figure 22A:
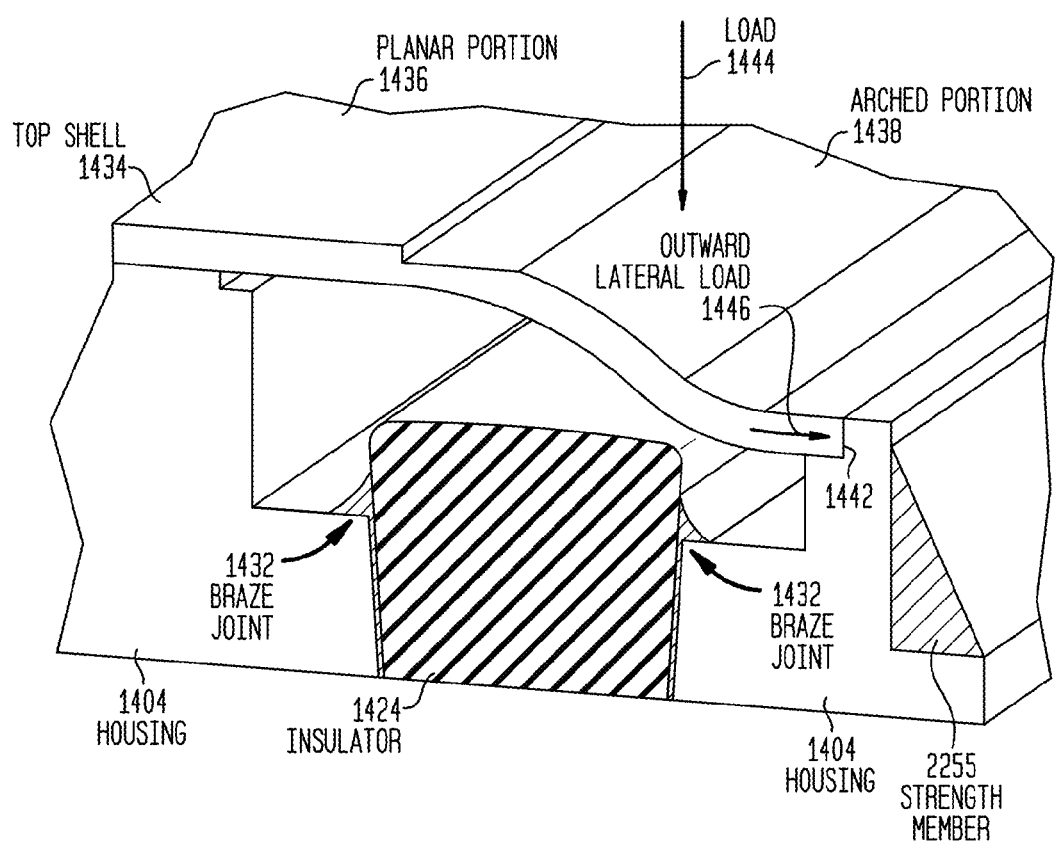
FIG. 22A is cross-sectional, perspective view of a portion of an implantable medical device in accordance with embodiments presented herein.

FIG. 22A illustrates one embodiment of an implantable medical device that includes a housing 1404 and top shell 1434 (as described above with reference to FIGS. 14A and 14B). As noted above, when load 1444 is applied, there is a tendency for the arched portion 1438 of top shell 1434 to straighten, thereby placing outward lateral load 1446 on housing 1404 at wall 1442. In the embodiments of FIG. 22A, a strength member 2255 is added (e.g., welded, stamped, integrated with, etc.) to the housing 1404 at a location so as to counter-act (i.e., oppose) the outward lateral load 1446. By counter-acting the outward lateral load 1446, no tensile load is transmitted to the braze joint 1432.

Figure 22B:
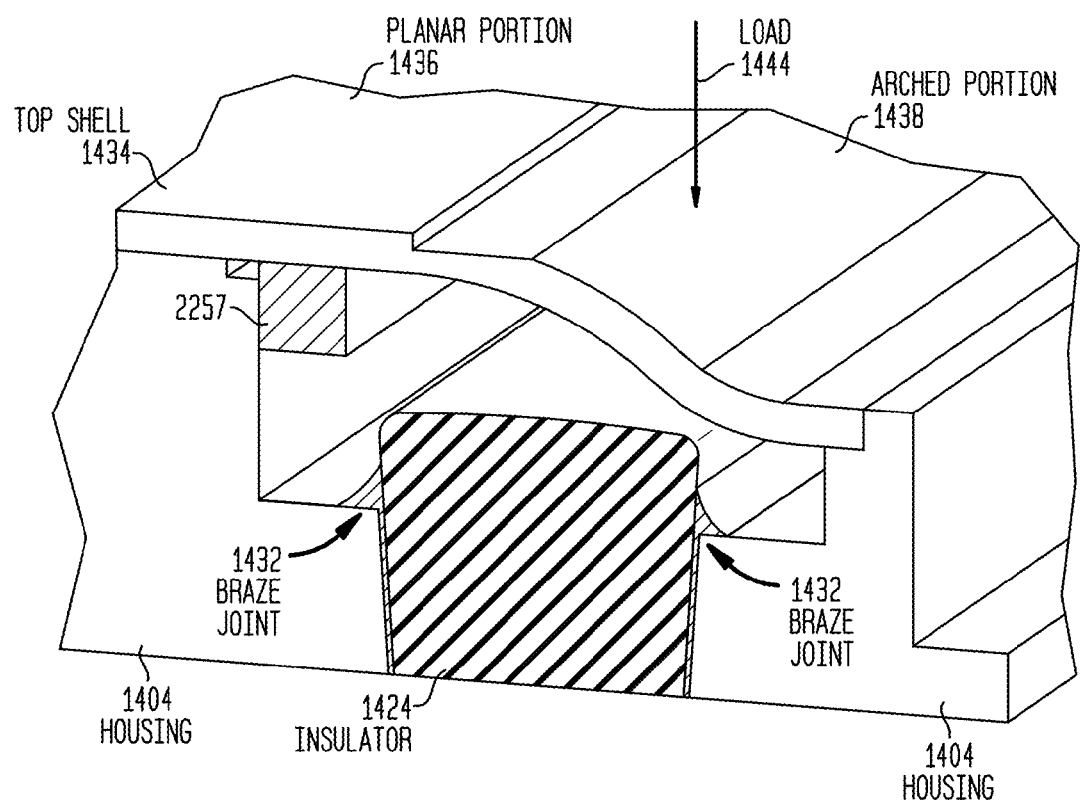
FIG. 22B is cross-sectional, perspective view of a portion of an implantable medical device in accordance with embodiments presented herein.
Figure 22D:
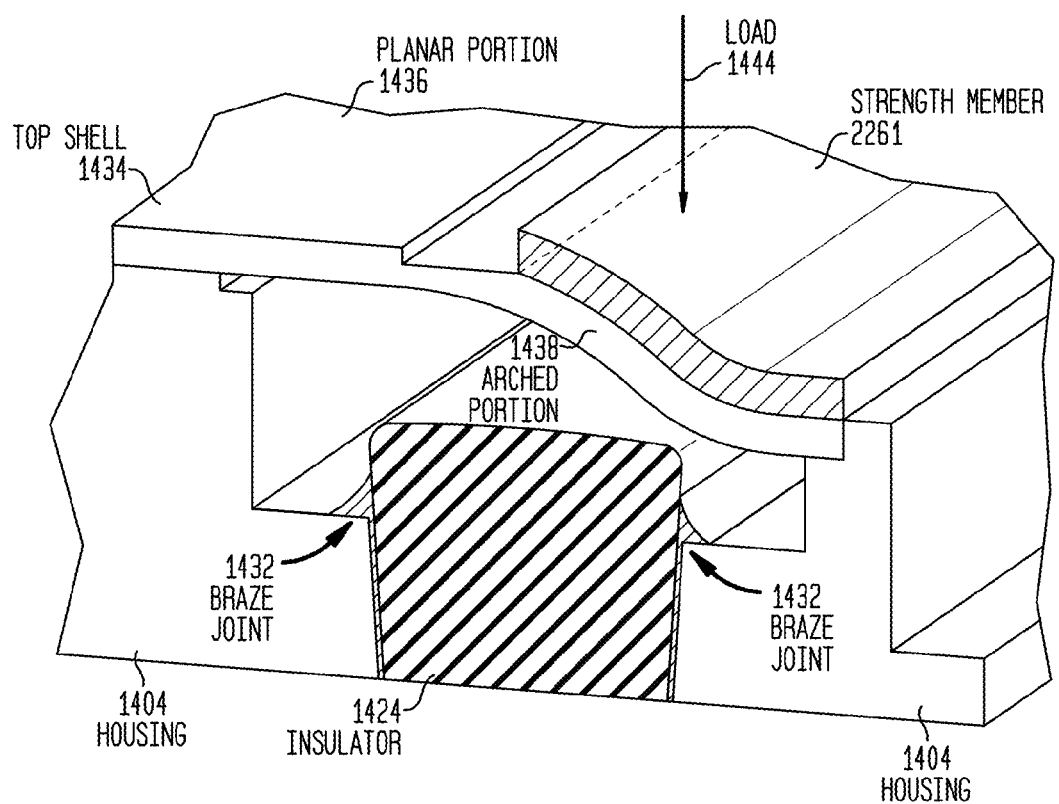
FIG. 22D is cross-sectional, perspective view of a portion of an implantable medical device in accordance with embodiments presented herein.

FIG. 22A illustrates one exemplary shape and location for a strength member to prevent application of a tensile load to the braze joint 1432. It is to be appreciated that strength members in accordance with embodiments presented herein may have a number of different sizes and locations. FIGS. 22B-22D illustrate the use of other strengths in accordance with such alternative embodiments.

More specifically, FIG. 22B illustrates the use of a strength member 2257 that is added underneath planar portion 1436. In the embodiments of FIG. 22B, the strength member 2257 may be attached to the housing 1404 and/or the planar portion 1436 and is configured to counteract the load 1444. In the embodiments of FIG. 22B, the strength member 2257 substantially reduces the tendency of the top shell to bend inwards.

FIG. 22C illustrates the use of a strength member 2259 that is added under arched portion 1438 adjacent to the outer edge of housing 1404. Similar to the embodiments of FIG. 22A, strength member 2259 is added to the housing 1404 and/or the arched portion 1438 so as to counter-act the outward lateral load 1446. More specifically, as the arched portion 1438 attempts to straighten, the arched portion 1438 will inherently bend inward. By adding the strength member 2259 beneath the arched portion 1438, the inward bending of the arched portion 1438 may be prevented, thereby preventing the straightening of the arched portion and application of the outward lateral load 1446.

It is to be appreciated that the strength member 2259 may have a number of different configurations. In one example, the strength member 2259 has a tripod shape and is disposed near a central portion of the housing wall 1442. In certain embodiments, the arched portion 1438 may be welded to the strength member 2259.

FIG. 22D illustrates one example shape, size, location, etc. for a strength member added to the arched portion 1428. It is to be appreciated that other strength member configurations (e.g., multiple strength members, stamped ribs, etc.) may be added to the arched portion 1428 in alternative embodiments. It is also to be appreciated that other mechanisms may be employed to stiffen the arched portion 1428 that aids in resisting the tendency to straighten following application of the load 1444. For example, in one alternative to the embodiments of FIG. 22D, rather than adding a strength member 2261 to the arched portion 1438, the thickness of the arched portion 1438 may be increased. The thickness of the arched portion 1438 may be increased so that the arched portion has an inherent stiffness that is sufficient to resist the tendency to straighten following application of the load 1444.

It is to be appreciated that the strength members of FIGS. 22A-22D may be formed from any material (e.g., titanium) that adds the desired strength and/or stiffness to the housing 1404 and/or the top shell 1434. It is also to be appreciated that the strength members of FIGS. 22A-22D are illustrative and that other strength members may be added to the housing and/or top shell to minimize tensile loading of a braze joint.

It is to be appreciated that changes to the manner by which the top shell is attached to the housing may also or alternatively be used to counter-act the arch effect. For example, in one embodiment additional welds may be added close to the planar portion of a top shell to resist the tendency to generate an outward lateral force in response to loading. Alternatively, the connection point between a top shell and a housing may be weaken or strengthened. Strengthening of the connection point may be used to counteract an outward lateral force, while weakening of the connection may be used to facilitate bending of crumpling of the top shell.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus comprising:
a housing having an aperture extending through the housing, wherein a housing sidewall substantially surrounds the aperture;
an insulator configured to be positioned in the aperture and comprising one or more conductors extending therethrough; and
a braze washer having a top flange configured to abut a surface of the housing and one or more first protrusions extending from the top flange and configured to be positioned in one or more indentations in at least one of the housing sidewall and the insulator such that the one or more first protrusions are disposed in the indentations between the insulator and the housing sidewall,
wherein the one or more first protrusions are configured to be positioned in the housing prior to positioning of the insulator in the aperture, and wherein the one or more first protrusions provide resistance during insertion of the insulator such that the insulator is press-fit into the aperture and the braze washer.

2. The apparatus of claim 1, wherein the top flange and the one or more first protrusions comprise a unitary element.

3. The apparatus of claim 1, wherein the braze washer further comprises one or more second protrusions configured to extend in a substantially opposite direction from the one or more first protrusions.

4. The apparatus of claim 1, wherein the one or more indentations comprise a single indentation substantially surrounding the aperture, and wherein the braze washer comprises a single first protrusion configured to be positioned in the single indentation so as to substantially fill the single indentation and surround the aperture.

5. The apparatus of claim 1, wherein each of the one or more first protrusions comprises a slanted segment extending from the top flange at an angle, and a linear segment connected to a distal end of the slanted segment so as to be substantially perpendicular to the top flange.

6. The apparatus of claim 1, wherein the insulator comprises:
one or more conductors extending therethrough from a first surface to a second surface, and
one or more braze-impediment features disposed at a location between an initial position of the braze washer and the first surface and configured to prevent melted braze material from flowing onto the first surface.

7. A method comprising:
forming a housing that includes an aperture extending through the housing, wherein a housing sidewall substantially surrounds the aperture;
positioning an insulator comprising one or more conductors extending therethrough in the aperture;
prior to positioning of the insulator in the aperture, positioning a braze washer having a top flange configured to abut a surface of the housing and one or more first protrusions extending from the top flange into the housing such that the one or more first protrusions are disposed in the indentations between the insulator and the housing sidewall, and wherein the one or more first protrusions provide resistance during insertion of the insulator such that the insulator is press-fit into the aperture and the braze washer; and
applying heat to melt the braze washer so as to form a hermetic joint between the insulator and the housing.

8. The method of claim 7, wherein the braze washer further comprises one or more second protrusions, and further comprising:
positioning the braze washer such that the second protrusions extend in a substantially opposite direction from the one or more first protrusions.

9. The method of claim 7, wherein the one or more indentations comprise a single indentation substantially surrounding the aperture, and wherein the one or more first protrusions comprise a single first protrusion, further comprising:
positioning the braze washer such that the single first protrusion substantially fills the single indentation substantially surrounding the aperture.

10. An apparatus comprising:
a housing having an aperture extending through the housing, wherein a housing sidewall substantially surrounds the aperture;
a braze washer initially positioned adjacent to the aperture at a surface of the housing, wherein prior to brazing the braze washer comprises a top flange configured to abut the surface of the housing and one or more first protrusions extending from the top flange such that the one or more first protrusions are disposed in indentations between the insulator and the housing sidewall; and
an insulator configured to be positioned in the aperture and joined to the housing via brazing that results in melting and flow of the braze washer, wherein the insulator comprises:
one or more conductors extending therethrough from a first surface to a second surface, and
one or more braze-impediment features disposed at a location between an initial position of the braze washer and the first surface and configured to prevent melted braze material from flowing onto the first surface.

11. The apparatus of claim 10, wherein the one or more braze-impediment features comprises one or more notches disposed on the cross-surface.

12. The apparatus of claim 10, wherein the one or more braze-impediment features comprises one or more overhangs disposed on the cross-surface.

13. The apparatus of claim 10, wherein the one or more braze-impediment features comprises a chamfered edge joining the cross-surface to first surface.

14. The apparatus of claim 10, wherein the first surface is a surface of the insulator disposed outside the housing.

15. The apparatus of claim 10, wherein the first surface is a surface of the insulator disposed inside the housing.

16. The apparatus of claim 6, wherein the one or more braze-impediment features comprises one or more notches disposed on the cross-surface.

17. The apparatus of claim 6, wherein the one or more braze-impediment features comprises one or more overhangs disposed on the cross-surface.

18. The apparatus of claim 6, wherein the one or more braze-impediment features comprises a chamfered edge joining the cross-surface to first surface.

19. The method of claim 7, wherein the top flange and the one or more first protrusions comprise a unitary element.

20. The method of claim 7, wherein each of the one or more first protrusions comprises a slanted segment extending from the top flange at an angle, and a linear segment connected to a distal end of the slanted segment so as to be substantially perpendicular to the top flange.

\* \* \* \* \*